US012774947B2

(12) United States Patent
Rahnboy et al.

(10) Patent No.: US 12,774,947 B2
(45) Date of Patent: Oct. 27, 2026

(54) METHOD AND ANALYZER FOR ANALYZING A BLOOD SAMPLE

(71) Applicant: HemoCue AB, Angelholm (SE)

(72) Inventors: Johan Rahnboy, Angelholm (SE); Joakim Pettersson, Angelholm (SE); Tomas Jonasson Bjarang, Angelholm (SE); Per Johansson, Angelholm (SE)

(73) Assignee: HemoCue AB, Ängelholm (SE)

(*) Notice: Subject to any disclaimer, the term of this patent is extended or adjusted under 35 U.S.C. 154(b) by 172 days.

(21) Appl. No.: 18/567,941

(22) PCT Filed: Dec. 20, 2022

(86) PCT No.: PCT/EP2022/086903
§ 371 (c)(1),
(2) Date: Dec. 7, 2023

(87) PCT Pub. No.: WO2023/118079
PCT Pub. Date: Jun. 29, 2023

(65) Prior Publication Data

US 2024/0280472 A1 Aug. 22, 2024

(30) Foreign Application Priority Data

Dec. 23, 2021 (EP) .................................... 21217560

(51) Int. Cl.
*G01N 21/07* (2006.01)
*G01N 1/40* (2006.01)
(Continued)

(52) U.S. Cl.
CPC ........... *G01N 21/07* (2013.01); *G01N 1/4077* (2013.01); *G01N 21/31* (2013.01); *G01N 33/491* (2013.01);
(Continued)

(58) Field of Classification Search
CPC ...... G01N 21/07; G01N 1/4077; G01N 21/31; G01N 33/491; G01N 2001/4083;
(Continued)

(56) References Cited

U.S. PATENT DOCUMENTS 4,088,448 A 5/1978 Lilja et al.
5,286,454 A 2/1994 Nilsson et al.
(Continued)

FOREIGN PATENT DOCUMENTS

EP 138152 B1 12/1988
EP 574393 B1 1/1996
(Continued)

OTHER PUBLICATIONS

Shin, Dong Ah et al., "Point-of-care testing of plasma free hemoglobin and hematocrit for mechanical circulatory support," Scientific Reports, vol. 11, pp. 1-9 (2021).
(Continued)

*Primary Examiner* — Melanie Brown
(74) *Attorney, Agent, or Firm* — FBT Gibbons LLP

(57) ABSTRACT

Disclosed is a method for analyzing a blood sample. The method comprises arranging a cuvette comprising a sampling cavity and a sample analysis cavity on a rotatable member. The sampling cavity comprises a blood sample to be analyzed. The method comprises rotating the rotatable member at a first speed in a first rotation cycle for transfer of the blood sample from the sampling cavity to the sample analysis cavity. The method comprises rotating the rotatable member at a second speed in a second rotation cycle after the first rotation cycle for separating blood parts from plasma in the blood sample. The method comprises obtaining, using a photometer, during the second rotation cycle, second absorbance data indicative of absorbance in the plasma. The method comprises determining, based on the second absor-
(Continued)

bance data, a second blood parameter being a plasma free hemoglobin level of the blood sample. The method comprises providing an output indicative of the second blood parameter.

23 Claims, 12 Drawing Sheets

(51) Int. Cl.
*G01N 21/31* (2006.01)
*G01N 33/49* (2006.01)

(52) U.S. Cl.
CPC ................ *G01N 2001/4083* (2013.01); *G01N 2201/062* (2013.01)

(58) Field of Classification Search
CPC ........... G01N 2201/062; G01N 21/255; G01N 15/05; G01N 33/721; G01N 2015/055; G06T 7/0012; G06T 2207/30024; B01L 2400/0409; B01L 3/502715; B01L 3/50273
See application file for complete search history.

(56) References Cited

U.S. PATENT DOCUMENTS

| | | | |
|---|---|---|---|
| 2005/0051466 A1 | 3/2005 | Carter et al. | |
| 2007/0259436 A1 | 11/2007 | Tarasev | |
| 2008/0138793 A1 | 6/2008 | Lindberg et al. | |
| 2009/0074620 A1 | 3/2009 | Therup et al. | |
| 2017/0326543 A1* | 11/2017 | Saiki | A61B 5/14532 |
| 2019/0170630 A1 | 6/2019 | Dayel et al. | |
| 2020/0256845 A1* | 8/2020 | Kjaer | G01N 21/31 |

FOREIGN PATENT DOCUMENTS

| | | | |
|---|---|---|---|
| EP | 470202 | B2 | 10/1997 |
| EP | 821784 | B1 | 11/1998 |
| EP | 0 965 388 | A2 | 12/1999 |
| EP | 1055111 | B1 | 2/2007 |
| EP | 1055112 | B1 | 2/2008 |
| EP | 2075567 | A2 | 7/2009 |
| EP | 1698883 | B1 | 1/2011 |
| EP | 3 312 586 | A1 | 4/2018 |
| EP | 3160645 | B1 | 2/2019 |
| GB | 2 525 622 | A | 11/2015 |
| WO | WO 2007/008137 | A1 | 1/2007 |
| WO | 2007111555 | A1 | 10/2007 |
| WO | 2008069720 | A1 | 6/2008 |
| WO | WO 2017/085180 | A1 | 5/2017 |
| WO | 2019207284 | A1 | 10/2019 |
| WO | 2022254175 | A1 | 12/2022 |
| WO | 2023175347 | A1 | 9/2023 |
| WO | 2023175349 | A1 | 9/2023 |
| WO | 2023175352 | A1 | 9/2023 |
| WO | 2023203315 | A1 | 10/2023 |
| WO | 2023203316 | A1 | 10/2023 |

OTHER PUBLICATIONS

International Search Report for International Application No. PCT/EP2022/086903, dated Feb. 21, 2023 (4 pages).
Written Opinion of the International Search Authority for International Application No. PCT/EP2022/086903 (5 pages).

* cited by examiner

METHOD AND ANALYZER FOR ANALYZING A BLOOD SAMPLE

This application is a national stage filing under 35 U.S.C. § 371 of International Application No. PCT/EP2022/086903, filed on Dec. 20, 2022, which claims priority to European Patent Application No. 21217560.8, filed on Dec. 23, 2021. The contents of these applications are each incorporated herein by reference in their entirety.

The present disclosure pertains to the field of blood analysis. The present disclosure relates to a method and an analyzer for analyzing a blood sample.

BACKGROUND

Hematology is a branch of medicine covering diseases related to the blood and its components, including methods of treatment, diagnosis, analysis, etc. Hematology encompasses a number of different assessments that can be performed on blood and/or components of the blood. One or more of the assessments could require preparation of a blood sample prior to the actual assessment.

Typical hematology analysis is performed in a laboratory setting and requires transportation of a blood sample to the laboratory. Thus, there is significant time delay between receiving a blood sample and providing analysis, which can slow down necessary patient care.

SUMMARY

Accordingly, there is a need for accurate and fast hematology analysis in order to quickly assess and analyze components of a patient's blood. In particular, there is a need for accurate and fast point-of-care hematology analysis. In particular, there is a need for accurate and fast point-of-care analysis of blood samples to determine the level of plasma free hemoglobin (PfHgb) in blood samples, i.e., blood samples from patients supported by an extracorporeal membrane oxygenation device (ECMO) or a ventricular assist device (VAD).

Disclosed is a method for analyzing a blood sample. The method comprises arranging a cuvette comprising a sampling cavity and a sample analysis cavity on a rotatable member. The sampling cavity comprises a blood sample to be analyzed. The method comprises, prior to the first rotation cycle, rotating the rotatable member at an initial speed in an initial rotation cycle, wherein the initial speed is insufficient for transfer of the blood sample from the sampling cavity to the sample analysis cavity. The method comprises obtaining, using a photometer, during the initial rotation cycle, initial absorbance data indicative of an absorbance in or through the sample analysis cavity of the cuvette. The method comprises determining, based on the initial absorbance data, a cuvette parameter associated with the cuvette. The method comprises, providing an output indicative of the cuvette parameter. The method comprises rotating the rotatable member at a first speed, such as a first maximum speed, in a first rotation cycle for transfer of the blood sample from the sampling cavity to the sample analysis cavity. The method comprises rotating the rotatable member at a second speed in a second rotation cycle after the first rotation cycle for separating blood parts from plasma in the blood sample. The method comprises obtaining, using a photometer, during or after the second rotation cycle, second absorbance data indicative of absorbance in the plasma. The method comprises determining, based on the second absorbance data, a second blood parameter being a plasma free hemoglobin level of the blood sample. The method comprises providing an output indicative of the second blood parameter.

It is an advantage of the present disclosure that a centrifugation of the blood sample and an analysis of the blood sample may be performed in a single method. Thereby, the time for performing the analysis can be reduced, since the cuvette comprising the blood sample does not have to be transported to different devices for performing centrifugation and analysis of the body fluid sample. Further, since the blood sample does not have to be transported between devices, such as between a centrifuge and an analyzing unit, the risk of contamination of the blood sample can be reduced thereby increasing the quality of the analysis. The method of the present disclosure further allows a plurality of blood parameters, such as total hemoglobin and plasma free hemoglobin to be determined in a continuous analysis cycle, without having to remove and/or replace the blood sample. It is thus an important advantage of the present disclosure that the method can provide fast and accurate analysis hematological analysis of a blood sample. Further, it is an important advantage that the method provides point-of-care hematological results, rather than having to transport the blood to a laboratory setting.

Disclosed is a blood analyzer comprising a housing, a rotatable member, a photometer, and a controller. The rotatable member being rotatably arranged in the housing and comprising a receptacle for receiving a cuvette comprising a sampling cavity and a sample analysis cavity. The receptable may either be an integral part of the rotatable member or may be a separate body attached to the rotatable member upon use. If the receptable is in the form of a separate body, the receptable may be detached from the rotatable member for replacement or for easy cleaning. The sampling cavity of the cuvette comprising a blood sample to be analyzed. The photometer is configured to obtain absorbance data associated with the sample analysis cavity of the cuvette. The controller is configured to, prior to the first rotation cycle, rotate the rotatable member at an initial speed in an initial rotation cycle, wherein the initial speed is insufficient for transfer of the blood sample from the sampling cavity to the sample analysis cavity. The controller is configured to control the photometer to obtain, during the initial rotation cycle, initial absorbance data indicative of an absorbance in the sample analysis cavity of the cuvette. The controller is configured to, determine, based on the initial absorbance data, a cuvette parameter associated with the cuvette. The controller is configured to provide an output indicative of the cuvette parameter. The controller is configured to rotate the rotatable member at a first speed, such as a first maximum speed, in a first rotation cycle for transfer of the blood sample from the sampling cavity to the sample analysis cavity. The controller is configured to rotate the rotatable member at a second speed in a second rotation cycle after the first rotation cycle for separating blood parts from plasma in the blood sample. The controller is configured to control the photometer to obtain, during or after the second rotation cycle, second absorbance data indicative of absorbance in the plasma of the separated blood sample. The controller is configured to determine, based on the second absorbance data, a second blood parameter being a plasma free hemoglobin level of the blood sample. The controller is configured to provide an output indicative of the second blood parameter.

It is an advantage of the present disclosure that a centrifugation of the blood sample and an analysis of the blood sample may be performed in a single analyzing device, since the cuvette comprising the blood sample does not have to be transported to different devices for performing centrifugation and analysis of the blood sample. Thereby, the time for performing the analysis can be reduced. Further, since the blood sample does not have to be transported between devices, such as between a centrifuge and an analyzing unit, the risk of contamination of the blood sample can be reduced thereby increasing the quality of the analysis. The analyzer of the present disclosure further allows a plurality of blood parameters, such as total hemoglobin and plasma free hemoglobin to be determined in a continuous analysis cycle, without having to remove and/or replace the body fluid sample. It is thus an important advantage of the present disclosure that the analyzer can provide fast and accurate analysis hematological analysis of a blood sample. Further, it is an important advantage of the analyzer that it provides point-of-care hematological results, rather than having to transport the blood to a laboratory setting.

BRIEF DESCRIPTION OF THE DRAWINGS

The above and other features and advantages of the present disclosure will become readily apparent to those skilled in the art by the following detailed description of exemplary embodiments thereof with reference to the attached drawings, in which.

DETAILED DESCRIPTION

Figure 1A:
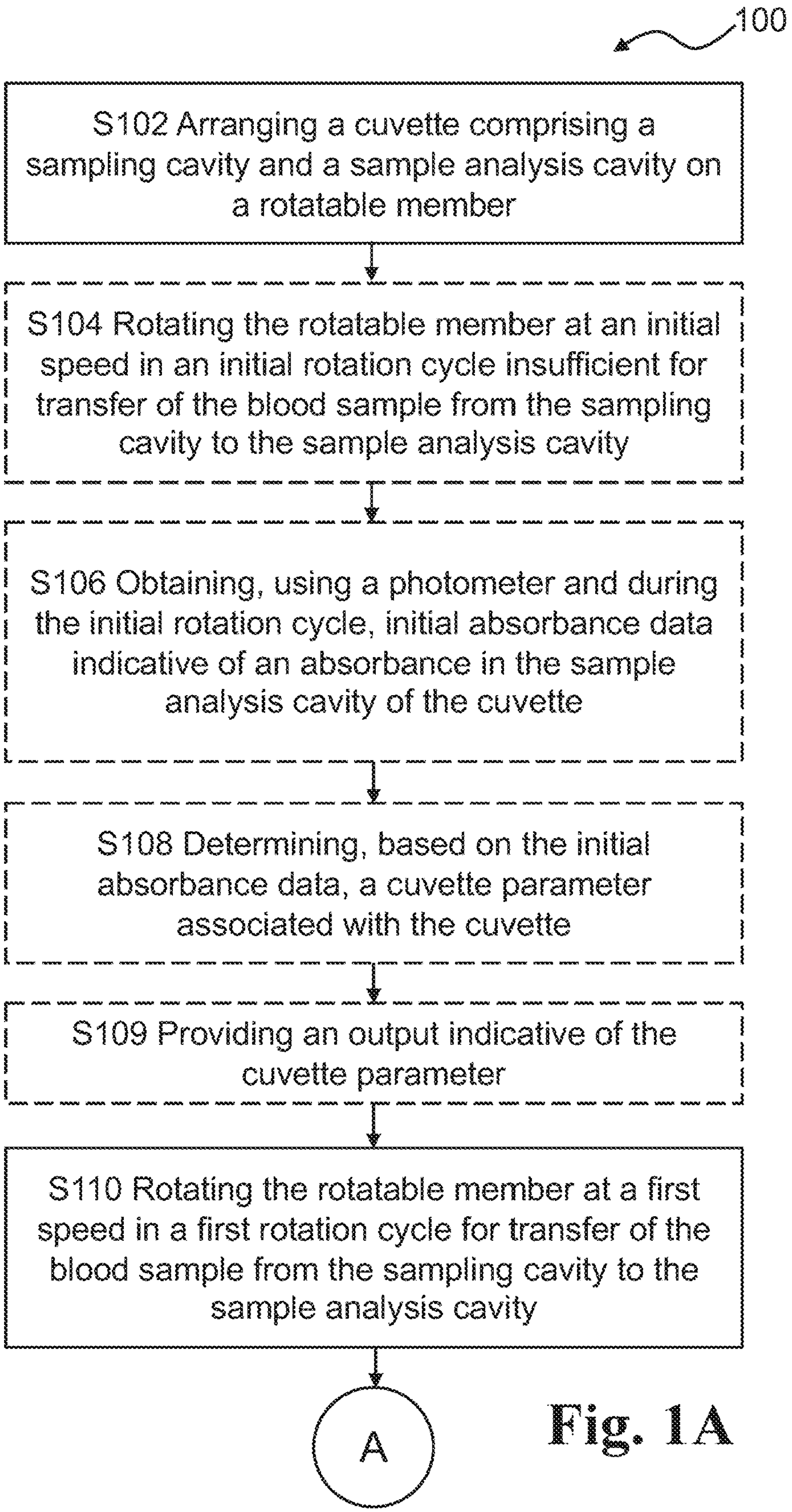
FIG. 1A-1D illustrate a method for analyzing a blood sample according to this disclosure.
Figure 1B:
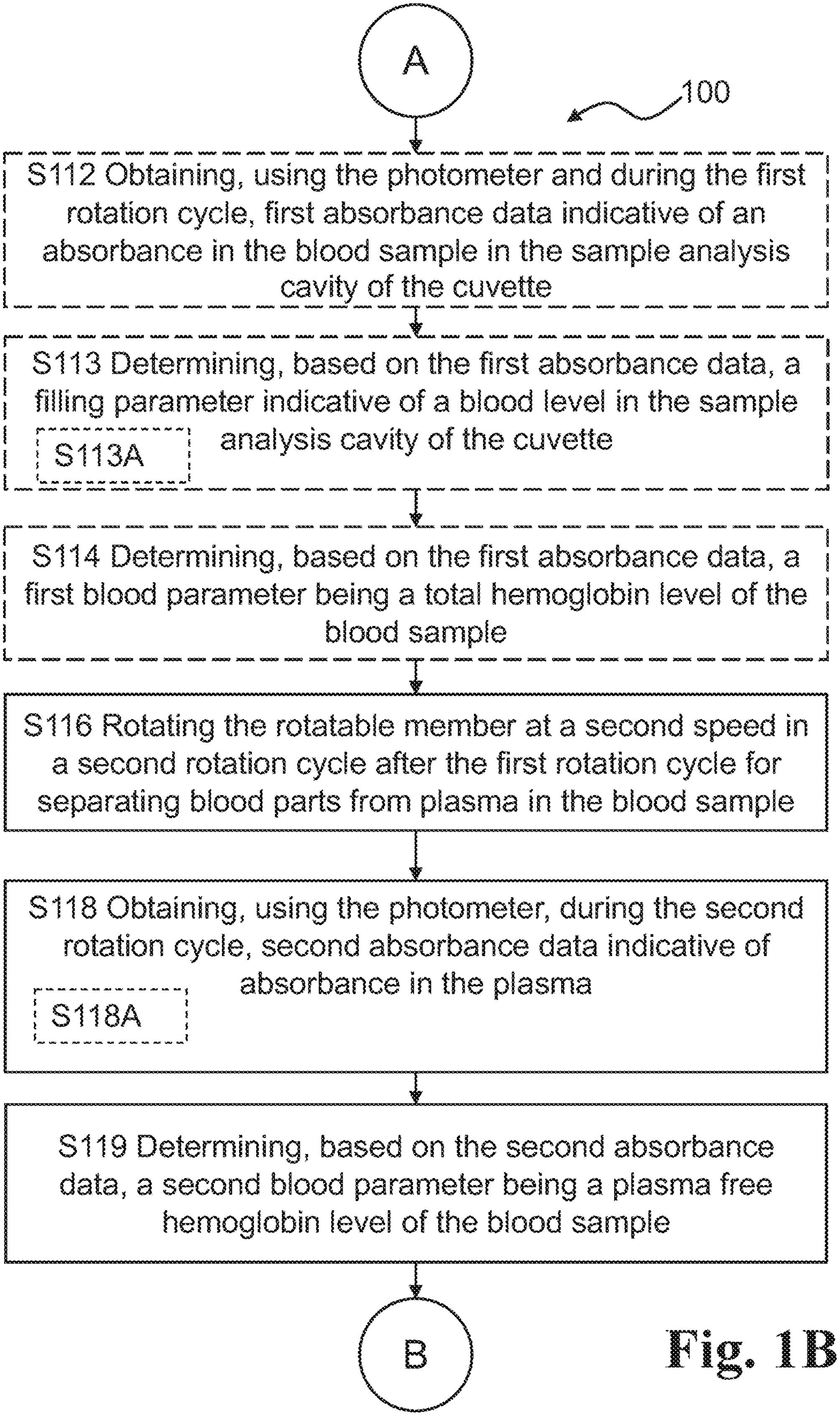
Figure 1C:
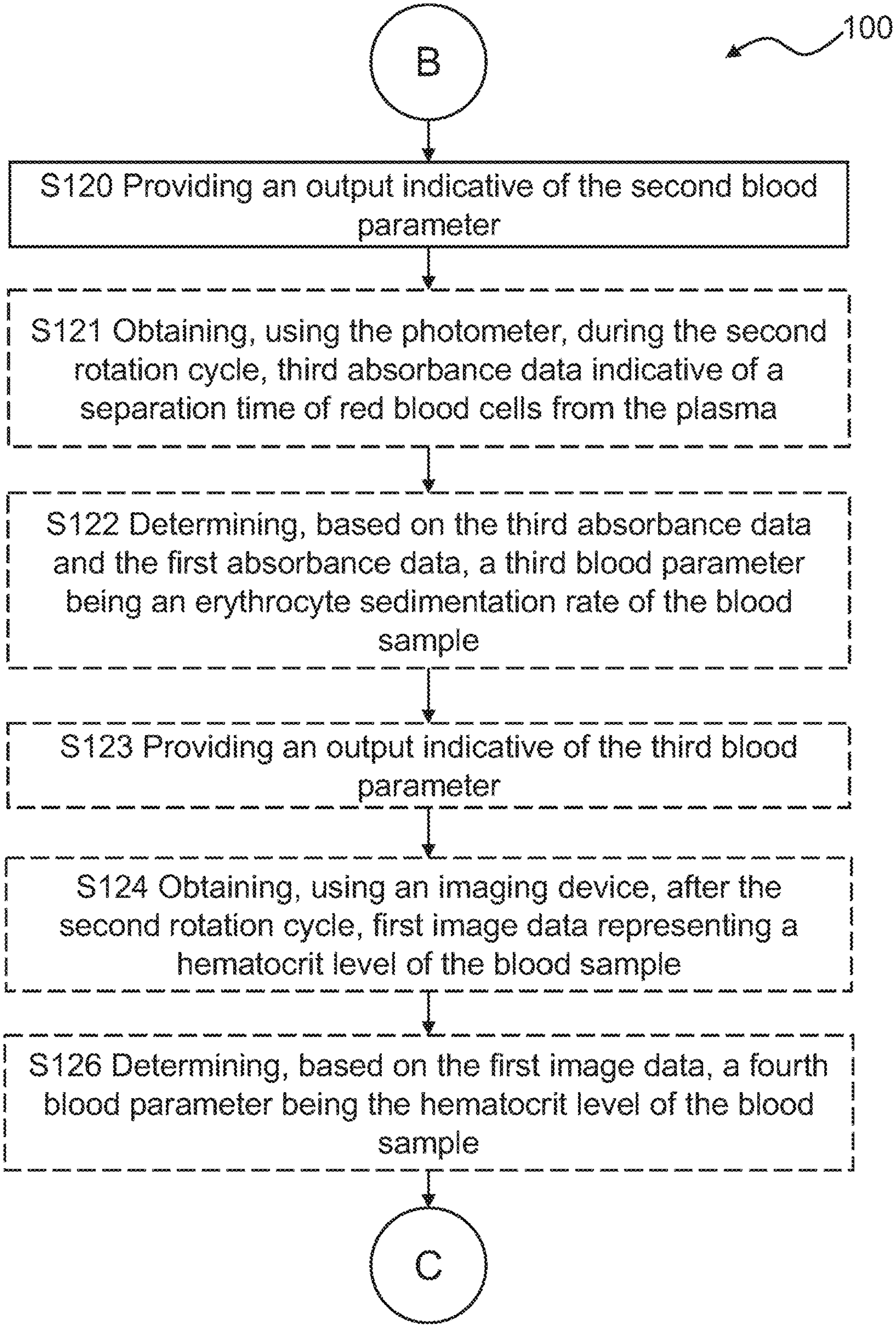
Figure 1D:
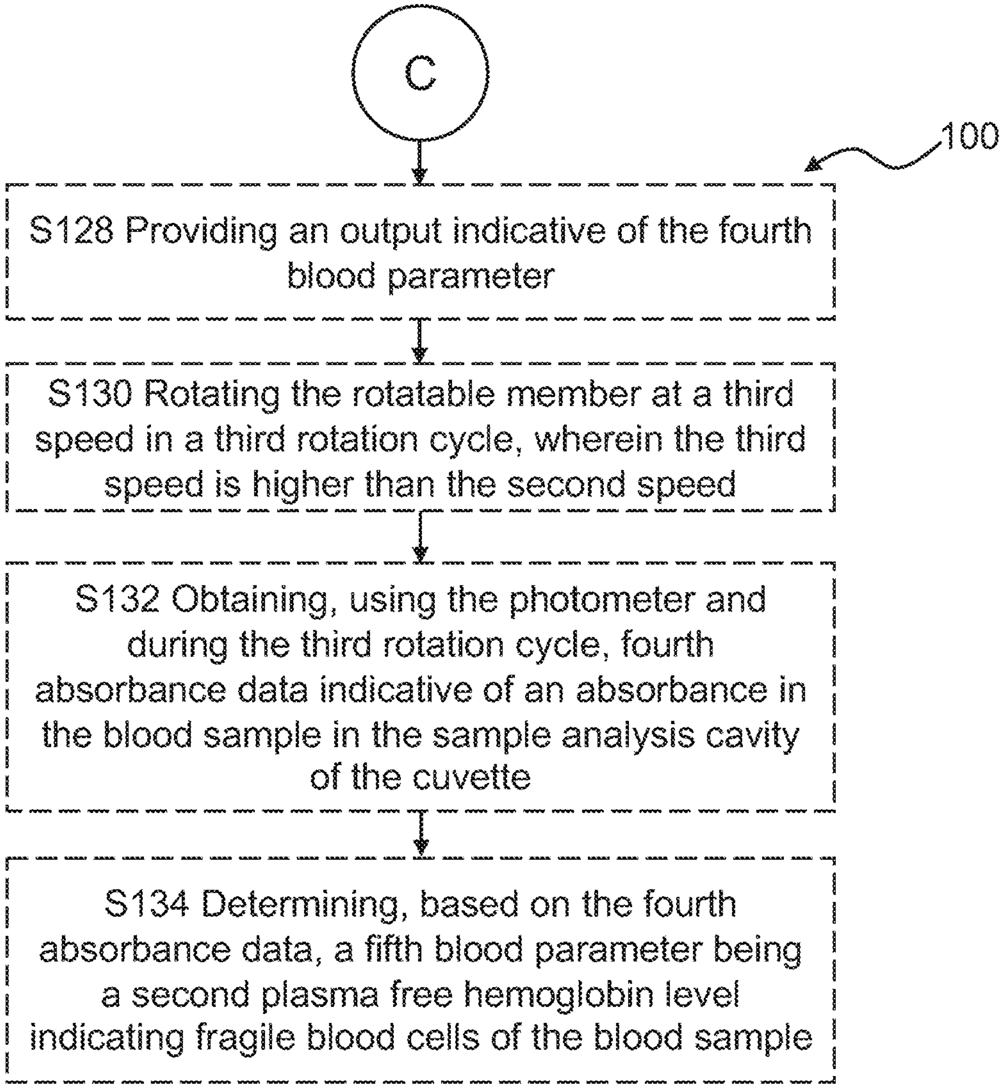

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the disclosure or as a limitation on the scope of the disclosure. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The figures are schematic and simplified for clarity, and they merely show details which aid understanding the disclosure, while other details have been left out. Throughout, the same reference numerals are used for identical or corresponding parts.

A method is disclosed for analyzing a blood sample. The method may be performed using a blood analyzer. A blood analyzer may herein be seen as an analysis apparatus for analysing blood.

The method comprises arranging a cuvette comprising a sampling cavity and a sample analysis cavity on a rotatable member. In one or more example methods, the cuvette comprises a sampling cavity, a venting cavity and a sample analysis cavity, e.g., as further described herein and illustrated in FIGS. 4-10. The sampling cavity comprises a blood sample to be analyzed. The method may comprise arranging the cuvette so that an opening of the cuvette is facing radially inwards towards a rotational axis of the rotating member and the sample analysis cavity of the cuvette is arranged radially outward from the sampling cavity of the cuvette.

In one or more example methods, the method may comprise rotating the rotatable member at an initial speed in an initial rotation cycle insufficient for transfer of the blood sample from the sampling cavity to the sample analysis cavity. The initial speed may create an initial centrifugal force acting on the blood sample during the initial rotation cycle that is below a capillary force acting on the blood sample in the sampling cavity. In other words, the initial speed is insufficient for transferring blood from the sampling cavity to the sample analysis cavity. Thereby, the blood sample will be held in the sampling cavity during initial rotation cycle. The sample analysis cavity will thus remain empty, wherein empty herein means not comprising any blood. In one or more example methods, the initial rotation cycle is performed prior to the first rotation cycle.

In one or more example methods, the method may comprise obtaining, using the photometer and during the initial rotation cycle, initial absorbance data indicative of an absorbance in or through the sample analysis cavity of the cuvette. Since the blood sample is held in the sampling cavity during the initial rotation cycle, the initial absorbance data may be absorbance data indicative of an absorbance through the empty sample analysis cavity. Obtaining the initial absorbance data may comprise measuring absorbance of the sample analysis cavity using one or more wavelengths, such as one, two, three, four, five, six or more wavelengths.

In one or more example methods, the method may comprise determining, based on the initial absorbance data, a cuvette parameter. The cuvette parameter may, in one or more example methods, be indicative of a contamination level associated with the cuvette. The contamination level associated with the cuvette may comprise, such as may be indicative of, scratches on the surface, such as on an inner surface and/or an outer surface, of the cuvette, discoloration of the cuvette, contamination of the cuvette, and/or any other imperfections of the cuvette, in the area of the sample analysis cavity of the cuvette. In other words, the contamination level associated with the cuvette may be indicative of defects of the cuvette, such as of the material or the surface of the cuvette, that may negatively affect the analysis of the blood sample. The contamination may for example be caused by blood, fingerprints or other debris added to the area of the sample analysis cavity due to incorrect handling of the cuvette by an operator. In one or more example methods, the cuvette parameter may indicate if a cuvette from a previous analysis has been replaced, or if an already centrifuged cuvette is present in the analyzer. The cuvette parameter may, in one or more example methods, indicate that no cuvette is present in the receptacle, such as whether a cuvette is present in the receptacle or not. The cuvette parameter may, in one or more example methods, be indicative of the initial absorbance data of the empty cuvette.

In one or more example methods, the method comprises providing an output indicative of the cuvette parameter. In one or more example methods, providing the output may comprise displaying a message to the operator indicative of the cuvette parameter. The message may for example indicate that the contamination level of the cuvette is equal to or above a predetermined contamination threshold or that the contamination level is below the predetermined contamination threshold. The contamination level being equal to or above the contamination threshold may indicate to the operator that an analysis of the blood sample using the cuvette cannot be performed. The contamination level being below the contamination threshold may indicate to the operator that the operator may proceed with the analysis of the blood sample using the cuvette. In one or more example methods, upon determining that the cuvette parameter is below a cuvette detection threshold, providing the output may comprise displaying a message indicating that no cuvette is detected. The cuvette detection threshold may be lower than the contamination threshold. In one or more example methods, providing the output may comprise providing the cuvette parameter to a compensation function which can compensate for the contamination level during subsequent measurements and determination of blood parameters using the cuvette.

The method comprises rotating the rotatable member at a first speed, such as a first maximum speed, in a first rotation cycle for transfer of the blood sample from the sampling cavity to the sample analysis cavity. The first speed, such as the first maximum speed, may be configured to create a first centrifugal force that is greater than a third capillary force produced by the sampling cavity of the cuvette. The first centrifugal force transfers the blood sample from the sampling cavity to the sample analysis cavity. In one or more example methods, the first rotation cycle is performed after the initial rotation cycle. The use of the terms “first speed” or “first rotation cycle” here does not imply any particular order in relation to the “second”, and “third” speed and/or “second”, and “third” rotation cycle, but are used to identify individual elements. In other words, in one or more example methods, the method may comprise a first rotation cycle without necessarily comprising a second rotation cycle and may be rotated at a first speed without necessarily having to be rotated at a second speed. However, in one or more example methods comprising a plurality of the rotation cycles described herein, it may be beneficial to perform the rotation cycles according to the order indicated by “first”, “second”, and/or “third”.

In one or more example methods, the method may comprise obtaining, using the photometer and during or after the first rotation cycle, first absorbance data indicative of an absorbance in the blood sample in the sample analysis cavity of the cuvette. Obtaining the first absorbance data may comprise measuring absorbance of the blood sample in the sample analysis cavity using two or more wavelengths, such as two, three, four, five, six or more wavelengths.

In one or more example methods, the method comprises determining, based on the first absorbance data, a filling parameter indicative of a blood level, such as indicative of a fill level, such as indicative of the amount of blood, in the sample analysis cavity of the cuvette. The filling parameter may, in one or more example methods, be indicative of one or more of the sample analysis cavity being underfilled, the sample analysis cavity being incorrectly filled, and the sample analysis cavity being correctly filled. In one or more example methods, the sample analysis cavity may be determined to be underfilled when the first absorbance data is below a first blood level threshold. A too low blood level, such as an underfilled cuvette, may cause the absorbance data to be lower than when the sample analysis cavity is correctly filled. The sample analysis cavity being incorrectly filled can herein be seen as not being filled with blood, such as being filled with a fluid other than blood.

In one or more example methods, the method comprises providing an output indicative of the filling parameter, such as indicative of the amount of blood, in the sample analysis cavity of the cuvette. In one or more example methods, the output may indicate that a further analysis of the blood sample is not possible, such as when the filling parameter indicates that the cuvette is underfilled, and/or incorrectly filled. In one or more example methods, the output may indicate that a further analysis of the blood sample is possible, such as when the filling parameter indicates that the cuvette is correctly filled. In one or more example methods, the output may be a signal preventing a further analysis of the blood sample, such as when the filling parameter indicates that the cuvette is underfilled and/or incorrectly filled. In one or more example methods, the output may be a signal allowing a further analysis of the blood sample, such as when the filling parameter indicates that the cuvette is correctly filled.

In one or more example methods, the method may comprise determining, based on the first absorbance data, a first blood parameter being a total hemoglobin level of the blood sample. In one or more example methods, the total hemoglobin level may be determined by measuring on an isobestic wavelength between oxyhemoglobin ($HbO_2$) and deoxyhemoglobin (Hb) and a compensation wavelength on an unaltered whole blood or plasma. In one or more example methods, the total hemoglobin level may be determined without measuring on an isobestic wavelength between oxyhemoglobin ($HbO_2$) and deoxyhemoglobin (Hb), by measuring using additional wavelengths and by calculating ratios of the measured wavelengths.

In one or more example methods, the method comprises providing an output indicative of the first blood parameter, such as indicative of the total hemoglobin level. Providing the output may comprise providing the output to a display for indicating the total hemoglobin level to the operator.

The method comprises rotating the rotatable member at a second speed, such as a second maximum speed, in a second rotation cycle for separating blood parts from plasma in the blood sample. The second rotation cycle may be performed after the first rotation cycle. The blood parts may be for example one or more of blood cells (such as red blood cells and/or white blood cells), fibrinogen, buffy coat, and lipids. In other words, the blood parts separated from the plasma may be one or more of blood cells, red blood cells, white blood cells, fibrinogen, buffy coat, and lipids. In one or more example methods, the second speed, such as the second maximum speed, is higher than the first speed, such as the first maximum speed. In one or more example methods, the second speed, such as the second maximum speed, may be equal to the first speed, such as the first maximum speed, and the second rotation cycle may be longer than the first rotation cycle. In other words, in order to separate the blood parts from the plasma, the rotatable member can be rotated at a higher second speed than the first speed or during a longer second rotation cycle than the first rotation cycle. The use of the terms “second speed” or “second rotation cycle” here does not imply any particular order in relation to the “first”, and “third” speed and/or “first”, and “third” rotation cycle, but are used to identify individual elements. In other words, in one or more example methods, the method may comprise a second rotation cycle without necessarily comprising a first rotation cycle and may be rotated at a second speed without necessarily having to be rotated at a first speed. However, in one or more example methods comprising a plurality of the rotation cycles described herein, it may be beneficial to perform the rotation cycles according to the order indicated by “first”, “second”, and/or “third”.

Fibrinogen is a glycoprotein complex, made in the liver, that circulates in the blood. During tissue and vascular injury, fibrinogen may be converted enzymatically by thrombin to fibrin and then to a fibrin-based blood clot. Fibrin clots function primarily to occlude blood vessels to stop bleeding. Buffy coat is the fraction of an anticoagulated blood sample that contains most of the white blood cells and platelets following centrifugation of the blood sample. Lipids are fats comprised in the blood.

The method comprises obtaining, using the photometer, during or after the second rotation cycle, second absorbance data. The second absorbance data being indicative of absorbance in the plasma. Obtaining the second absorbance data may comprise measuring absorbance of the plasma in the sample analysis cavity using two or more wavelengths, such as two, three, four, five, six or more wavelengths.

The method comprises determining, based on the second absorbance data, a second blood parameter. The second blood parameter being a plasma free hemoglobin (PfHgb) level of the blood sample. In one or more example methods, the second absorbance data, such as the plasma free hemoglobin level, can be obtained continuously during the second rotation cycle to detect when all, such as substantially all, blood cells have left the measuring eye and the remaining sample material is substantially pure plasma (with potential free hemoglobin), and the photometer detects a stable detection signal, such as a signal indicating stable, such as non-changing, absorbance data. During the second rotation cycle the plasma and the blood parts, such as one or more of blood cells, fibrinogen, buffy coat, and lipids, will continuously separate from each other, thereby the obtained absorbance data will continuously change. When the plasma and the blood parts, such as one or more of blood cells, fibrinogen, buffy coat, and lipids, are fully separated, the absorbance data will stop changing and a stable absorbance data can be detected. The absorbance data being stable is thus indicative of the separation being finished. Upon detecting that the detection signal, such as the obtained second absorbance data, is stable the obtained PfHgb level may be presented. Upon detecting that the detection signal is stable, the obtaining of the second absorbance data may be ended. Ending the obtaining of the second absorbance data may comprise one or more of stopping the second rotation cycle, reducing the speed of the second rotation cycle, obtaining third absorbance data and/or first imaging data, and proceeding with another rotation cycle, such as a third rotation cycle as described herein. By ending the obtaining of the second absorbance data upon detecting that the detection signal is stable a turnaround time (TAT) of the analysis may be reduced compared to when a pre-determined measuring time is used.

The rotation cycles defined herein may, in one or more example methods, be defined by the maximum speed allowed during the respective rotation cycle. For example, the initial maximum speed, may be lower than the first maximum speed, which is lower than the second maximum speed, which in turn is lower than the third maximum speed. However, the speed, such as the rotational speed of the rotatable member, may vary during each respective rotation cycle.

In one or more example methods, the rotatable member may be stopped between the different rotation cycles, such as the initial rotation cycle, the first rotation cycle, the second rotation cycle, and/or the third rotation cycle. In other words, the different rotation cycles may be separated by a period where the rotatable member is stationary. The rotation of the rotatable member may thus be interrupted between the rotation cycles.

In one or more example methods, the rotatable member may transition between the different rotation cycles, such as the initial rotation cycle, the first rotation cycle, the second rotation cycle, and/or the third rotation cycle, without being stopped. In other words, the rotatable member may transition between the different rotation cycles while continuously rotating. The initial rotation cycle, the first rotation cycle, the second rotation cycle, and/or the third rotation cycle may thus be seen as sub cycles within one continuous rotation cycle.

The method comprises providing an output indicative of the second blood parameter. In one or more example methods, providing the output may comprise providing an indication to the operator, the indication being indicative of the second blood parameter, such as of the PfHgb level of the blood sample. Providing the indication may comprise displaying a message to the operator indicative of the PfHgb level.

In one or more example methods, the method may comprise obtaining, using the photometer, during the second rotation cycle, third absorbance data. The third absorbance data may be indicative of a separation time of red blood cells from the plasma. Obtaining the third absorbance data may comprise measuring absorbance of the blood sample in the sample analysis cavity using two or more wavelengths, such as two, three, four, five, six or more wavelengths.

In one or more example methods, the method may comprise determining, based on the third absorbance data and the first absorbance data, a third blood parameter being an erythrocyte sedimentation rate (ESR) of the blood sample. The ESR is a type of blood test that measures how quickly red blood cells, which are also referred to as erythrocytes, settle at the bottom of a test tube, such as the cuvette, that contains the blood sample. Normally, red blood cells settle relatively slowly. A faster-than-normal rate may indicate inflammation in the body. Inflammation is part of your immune response system. It can be a reaction to an infection or injury.

In one or more example methods, the method may comprise providing an output indicative of the third blood parameter. In one or more example methods, providing the output may comprise providing an indication to an operator of the blood analyzer. Providing the indication may comprise displaying a message to the operator indicative of the third blood parameter. The message may for example indicate that the ESR is higher or lower than an ESR threshold.

The ESR threshold may be an ESR indicative of a normal ESR, such as an ESR range, for a healthy person.

In one or more example methods, the method may comprise obtaining, using an imaging device, after the second rotation cycle, first image data. Obtaining first image data may comprise capturing the first image data using the imaging device. The first image data may represent an image of at least a part of the blood sample in the sample analysis cavity, such as an interface between separated blood cells and separated plasma of the blood sample. The first image data may represent a position of the interface along a length of the sample analysis cavity, such as a percentual position along the length of the sample analysis cavity. The imaging device may be a camera.

In one or more example methods, the method may comprise determining, based on the first image data, a fourth blood parameter. The fourth blood parameter may be the hematocrit level of the blood sample. To determine the hematocrit level, the first image data should represent at least the part of blood sample where an interface between, on the one hand, the plasma, (such as the blood plasma) and, on the other hand, the red blood cell, is anticipated. The first imaging data may be indicative of a position of the interface between the separated red blood cells, and the blood plasma in the sample analysis cavity. In one or more example methods, such an interface is anticipated in the range of 30-60% of the length of the sample analysis cavity. In one or more example methods, the hematocrit level may be determined based on the position of the interface, where the percentual position of the interface along the length of the sample analysis cavity may be indicative of the percentual level of hematocrit. A low or a high hematocrit level with the same PfHgb concentration may be indicative of a more severe patient condition which may require further medical investigation.

In one or more example methods, the method may comprise providing an output indicative of the fourth blood parameter.

In one or more example methods, the method may comprise rotating the rotatable member at a third speed, such as a third maximum speed, in a third rotation cycle, wherein the third speed, such as the third maximum speed, is higher than the first speed, such as the first maximum speed, the second speed, such as the second maximum speed, and the initial speed, such as the initial maximum speed. The third rotation cycle may be performed after the second rotation cycle. The third speed may be configured to provoke degradation of fragile red blood cells. The use of the terms “third speed” or “third rotation cycle” here does not imply any particular order in relation to the “first” and “second” speed and/or “first” and “second” rotation cycle, but are used to identify individual elements. In other words, in one or more example methods, the method may comprise a third rotation cycle without necessarily comprising a first and/or a second rotation cycle and may be rotated at a third speed without necessarily having to be rotated at a first and/or a second speed. However, in one or more example methods comprising a plurality of the rotation cycles described herein, it may be beneficial to perform the rotation cycles according to the order indicated by “first”, “second”, and/or “third”.

In one or more example methods, the method may comprise obtaining, using the photometer and during the third rotation cycle, fourth absorbance data indicative of an absorbance in the blood sample in the sample analysis cavity of the cuvette. Obtaining the fourth absorbance data may comprise measuring absorbance of the blood sample in the sample analysis cavity using two or more wavelengths, such as two, three, four, five, six or more wavelengths.

In one or more example methods, the method may comprise determining, based on the fourth absorbance data, a fifth blood parameter. The fifth blood parameter may be a second plasma free hemoglobin level indicating fragile blood cells of the blood sample.

The difference between the second plasma free hemoglobin level and the first plasma free hemoglobin level indicates the level of fragile red blood cells, which may also be referred to as erythrocyte fragility or erythrocyte mechanical fragility), in the blood sample. The level of fragile red blood cells may be indicative of further medical disorders, such as Sickle Cell or Thalassemia.

In one or more example methods, the method comprises providing an output indicative of the fifth blood parameter. In one or more example methods, providing the output may comprise displaying a message to an operator indicative of the fifth blood parameter. The message may for example indicate that and give the operator an indication that further medical investigation is needed, such as for disorders like Sickle Cell and/or Thalassemia.

In one or more example methods, an error code may be indicated to the operator when an obtained absorbance level is indicative of a too high hematocrit level instead of providing erroneous results. This may for example be the case when the amount of blood cells is so large that it is not possible to gain sufficient amount of plasma, thereby leading to unwanted blood cells in an area of the sample analysis cavity of the cuvette covered by the photometer.

In one or more example methods, the method may comprise detection of various kind of erroneous filled cuvette and/or air bubbles in the blood sample based on one or more of the initial absorbance data, first absorbance data, second absorbance data, third absorbance data, first image data and fourth absorbance data. In one or more example methods, the method comprises determining, based on the first absorbance data, a blood level parameter indicative of a blood level, such as indicative of a fill level, in the sample analysis cavity of the cuvette. The blood level parameter may, in one or more example methods, be indicative of one or more of the sample analysis cavity being underfilled, the sample analysis cavity being overfilled, and the sample analysis cavity being correctly filled.

In one or more example methods, obtaining initial absorbance data, first absorbance data, second absorbance data, third absorbance data and/or fourth absorbance data comprises measuring absorbance using one, two, or more than two wavelengths, such as three wavelengths, four wavelengths, five wavelengths, six wavelengths or more. The wavelengths may be selected from a range between 300 nm and 1000 nm. In one or more example methods, the wavelengths may be two or more of 355 nm, 360 nm, 365 nm, 385 nm, 390 nm, 392 nm, 451 nm, 452 nm, 455 nm, 584 nm, 585 nm, 590 nm, 655 nm and 860 nm. However, other wavelengths selected from the range indicated above may also be used.

In one or more example methods, the absorbance data may be measured using a first wavelength, a second wavelength, a third wavelength and a fourth wavelength. In one or more example methods, the first wavelength is 585 nm, the second wavelength is 860 nm, the third wavelength is 385 nm and the fourth wavelength is 655 nm. In one or more example methods, the first wavelength is 585 nm, the second wavelength is 860 nm, the third wavelength is 455 nm and the fourth wavelength is 655 nm.

In one or more example methods, obtaining initial absorbance data, first absorbance data, second absorbance data, third absorbance data or fourth absorbance data comprises measuring absorbance data during a plurality of revolutions of the rotatable member.

In one or more example methods, determining one or more of the first blood parameter, the second blood parameter, the third blood parameter, the fourth blood parameter, the fifth parameter and the cuvette parameter comprises integrating absorbance data obtained during a plurality of revolutions of the rotatable member.

When measuring at high rotational speeds of the rotational member, there will be a very short time during each revolution when the cuvette is presented in a light path of the photometer. There is thus a limited time each revolution during which the photometer can obtain absorbance data from the cuvette and/or from the blood sample in the cuvette. To ensure that sufficient absorbance data for analyzing the blood sample is obtained, measured data from subsequent rotations may be stored and integrated over the rotations. Thereby, the more rotations the rotatable member does, the larger the obtained signal can be. When a sufficient signal has been obtained over a number of rotations, the integration may be stopped and a digitalization, such as an analog to digital (A/D) conversion to obtain an intensity value, such as the absorbance value of the measurements.

The initial rotation cycle, the first rotation cycle, the second rotation cycle and/or the third rotation cycle may be performed sequentially. Thereby, a plurality of blood parameters, such as the first, the second, the third, the fourth and/or the fifth blood parameter, such as the plasma free hemoglobin, the total hemoglobin, the sedimentation rate in the whole blood, in such system. may be obtained in a continuous analysis using a single blood sample, thus providing faster and more accurate results.

A blood analyzer is disclosed. The blood analyzer comprising a housing, a rotatable member, a photometer, and a controller. In one or more example blood analyzers, the blood analyzer may comprise a display configured to visually provide information to an operator of the blood analyzer, such as for visually displaying information indicative of the cuvette parameter, the first blood parameter, the second blood parameter, the third blood parameter, the fourth blood parameter, and/or the fifth blood parameter. In one or more example blood analyzers, the blood analyzer can comprise a drive unit, such as an electric motor, for driving, such as rotating the rotatable member.

The housing may be a single housing. The housing can accommodate any and/or all of the modules discussed herein, such as the rotatable member, the photometer, the controller, the display and/or the drive unit.

The housing may be plastic, metal, ceramic, etc. or combinations thereof, and the particular material of the housing is not limiting. The housing may include one or more ports. The housing may include one or more slots. The housing may include one or more vents. The housing may be a frame for holding the different modules, such as parts, of the blood analyzer.

The rotatable member is rotatably arranged in the housing. The rotatable member may be rotatably arranged around a rotational axis. The rotatable member comprises a receptacle for receiving a cuvette. The receptable may either be an integral part of the rotatable member or may be a separate body attached to the rotatable member upon use. If the receptable is in the form of a separate body, the receptable may be detached from the rotatable member for replacement or for easy cleaning. In one or more example analyzers, the receptacle may be configured to receive a cuvette having a specific shape or form. In one or more example analyzers, the receptacle may be selected from a plurality of different receptacles for receiving a respective type of cuvette. In one or more example analyzers, the rotatable member may be detached from the analyzer for replacement or for easy cleaning. In one or more example analyzers, the rotatable member may be selected from a plurality of rotatable members comprising different receptacles for receiving a respective type of cuvette. The cuvette may comprise a sampling cavity and a sample analysis cavity, the sampling cavity of the cuvette comprising a blood sample to be analyzed. The rotatable member may be a circular member, such as a disc. The receptacle may be arranged at a distance r from the rotational axis on the rotatable member, such that a centrifugal force $F=m\omega^2 r$ is exerted on a cuvette placed in the receptacle, where m is the mass of the cuvette, ris the distance from the rotational axis of the rotatable member and w is an angular velocity, such as the speed, at which the rotatable member is rotating.

The analyzer may comprise a drive unit, such as an electrical motor, for rotating the rotatable member. The controller may be configured to control the drive unit to control the speed of the rotatable member. In one or more example blood analyzers, the controller can include a computer program product. The computer program product can include a non-transitory computer readable medium. The non-transitory computer readable medium can have thereon a computer program. The computer program can include program instructions. The computer program can be loadable into a data processing unit. The computer program can be configured to cause execution of the steps, processes, and/or modules discussed above. For example, when the computer program is run by a data processing unit.

The rotatable member may comprise a measuring eye, such as an opening, for allowing light, such as light from a light source, to pass through the rotatable member. The opening may be arranged in the receptacle so that it overlaps with the sample analysis cavity of the cuvette, when the cuvette is arranged in the receptacle. In one or more example analyzers, the rotatable member may comprise a blanking hole for measuring an intensity of the light source, such as of an LED. The blanking hole may be a throughgoing hole arranged in the rotatable member for allowing light from the light source to pass through the rotatable member to the photometer. The blanking hole may be arranged at the same radial distance from the rotational center of the rotatable member as the measuring eye but with an angular displacement. In one or more example analyzers, the blanking hole may be arranged 180 degrees displaced from the measuring eye. This allows the photometer to alternately measure on the sample analysis cavity and the intensity of the light source at equal time intervals. By measuring the intensity of the light source through the blanking hole, a drifting of the light intensity of the light source can be detected, which can be used for compensating for the drifting light intensity during measurements on the sample analysis cavity.

The photometer may be a multi-wavelength photometer. The photometer may comprise a plurality of light sources, such as two or more light sources, for emitting light at respective wavelengths and one or more optical sensors, such as photo diodes, for measuring how much light is absorbed by an object located between the plurality of light sources and the one or more optical sensors. The plurality of light sources and the one or more optical sensors may be arranged on opposite sides of the rotatable member, such that the light emitted from the light sources passes through the opening in the rotatable member and the cuvette arranged in the receptacle of the rotatable member before it reaches the optical sensors. In other words, the plurality of light sources may be arranged on a first side of the rotatable member and the one or more optical sensors may be arranged on a second side of the rotatable member. The first side of the rotatable member and the second side of the rotatable member may be opposite sides of the rotatable member. The photometer may comprise a respective optical sensor for each of the light sources or may comprise one optical sensor for a plurality of light sources. In one or more example blood analyzers, the plurality of light sources, such as the two or more light sources, are Light Emitting Diodes (LEDs). In one or more example blood analyzers, the photometer may comprise a plurality of first light guides for directing the light emitted by the plurality of light source to the cuvette, and one or more second light guides for directing the light passing through the cuvette to the one or more optical sensors. In one or more example blood analyzers, the photometer comprises at least two light sources and at least two corresponding optical sensors, each light source emitting light at a different wavelength.

The photometer is configured to obtain, such as measure, the absorbance data associated with the sample analysis cavity of the cuvette.

In one or more example blood analyzers, the blood analyzer comprises a display for displaying, such as visually providing, information to an operator of the blood analyzer.

An advantage of the analyzer disclosed herein is thus that a centrifugation of the blood sample and an analysis of the blood sample may be performed in a single device. Thereby, the time for performing the analysis can be reduced. Further, since the blood sample does not have to be transported between devices, such as between a centrifuge and an analyzing unit, the risk of contamination of the blood sample can be reduced thereby increasing the quality of the analysis.

The controller is configured to rotate the rotatable member at a first speed, such as a first maximum speed, in a first rotation cycle for transfer of the blood sample from the sampling cavity to the sample analysis cavity. The controller may be configured to control the drive unit to rotate the rotatable member at the first speed, such as at the first maximum speed. The first speed, such as the first maximum speed, may be configured to create a first centrifugal force that is greater than a capillary force produced by the sampling cavity of the cuvette. The capillary force of the sampling cavity is herein referred to as a third capillary force in relation to the cuvette described herein. The first centrifugal force transfers the blood sample from the sampling cavity to the sample analysis cavity.

The controller may be configured to control the photometer to obtain, during the first rotation cycle, first absorbance data indicative of an absorbance in the blood sample in the sample analysis cavity of the cuvette. The controller may be configured to obtain the first absorbance data by controlling the photometer to measure absorbance of the blood sample in the sample analysis cavity using two or more wavelengths, such as two, three, four, five, six or more wavelengths.

The controller may be configured to determine, based on the first absorbance data, a first blood parameter being a total hemoglobin level of the blood sample. The controller may be configured to determine the total hemoglobin level by measuring, using the photometer, on an isobestic wavelength between oxyhemoglobin ($HbO_2$) and/or deoxyhemoglobin (Hb) and/or a compensation wavelength on an unaltered whole blood or plasma. In one or more example analyzers, the controller may be configured to determine the total hemoglobin level by measuring using additional, such as a plurality of wavelengths, and by calculating ratios of the measured wavelengths. The controller may thus, in one or more example analyzers, be configured to determine the total hemoglobin level without measuring on an isobestic wavelength between oxyhemoglobin ($HbO_2$) and deoxyhemoglobin (Hb).

In one or more example blood analyzers, the controller is configured to provide an output indicative of the first blood parameter.

The controller is configured to rotate the rotatable member at a second speed, such as a second maximum speed, in a second rotation cycle after the first rotation cycle for separating blood parts from plasma in the blood sample. The blood parts separated from the plasma may be one or more of blood cells, red blood cells, white blood cells, fibrinogen, buffy coat, and lipids.

The controller is configured to control the photometer to obtain, during the second rotation cycle, second absorbance data indicative of absorbance in the plasma of the separated blood sample. The controller may be configured to control the photometer to obtain the second absorbance data by measuring absorbance of the plasma in the sample analysis cavity using two or more wavelengths, such as two, three, four, five, six or more wavelengths.

The controller is configured to determine, based on the second absorbance data, a second blood parameter. The second blood parameter may be a plasma free hemoglobin (PfHgb) level of the blood sample. The controller may be configured to detect when all blood cells have left the measuring eye by being configured to detect that a stable detection signal, such as a stable second absorbance data, is provided from the photometer, such as signal indicating a stable, such as non-changing, absorbance data.

In one or more example analyzers, the controller may be configured to control the photometer and/or the rotatable member to continuously obtain second absorbance data during the second rotation cycle to detect when all, such as substantially all, blood cells have left the measuring eye and the remaining sample material is substantially pure plasma (with potential free hemoglobin). Upon detecting that a detection signal, such as the obtained second absorbance data, is stable, such as is non-changing. The controller may be configured to provide the obtained PfHgb level. Upon detecting that the detection signal is stable, the controller may be configured to end the obtaining of the second absorbance data. Ending the obtaining of the second absorbance data may comprise one or more of stopping the second rotation cycle, reducing the speed of the second rotation cycle, obtaining third absorbance data and/or first imaging data, and proceeding with another rotation cycle, such as a third rotation cycle as described herein. By ending the obtaining of the second absorbance data upon detecting that the detection signal is stable a turnaround time (TAT) can be reduced compared to what can be achieved when a predetermined measuring time is used.

The controller is configured to provide an output indicative of the second blood parameter. In one or more example methods, the controller may be configured to control a display unit to provide an indication to the operator indicative of the second blood parameter, such as the PfHgb level.

In one or more example blood analyzers, the controller is configured to rotate the rotatable member at an initial speed in an initial rotation cycle insufficient for transfer of the blood sample from the sampling cavity to the sample analysis cavity.

In one or more example blood analyzers, the controller is configured to control the photometer to obtain, during the initial rotation cycle, initial absorbance data indicative of an absorbance in the sample analysis cavity of the cuvette. In one or more example blood analyzers, the controller is configured to the controller is configured to perform the initial rotation cycle prior to the first rotation cycle.

In one or more example blood analyzers, the controller is configured to determine, based on the initial absorbance data, a cuvette parameter being, such as being indicative of, a contamination level associated with the cuvette. The contamination level associated with the cuvette may comprise scratches on the surface of the cuvette, discoloration of the cuvette or contamination of the cuvette in the area of the sample analysis cavity of the cuvette.

In one or more example blood analyzers, the controller is configured to provide an output indicative of the cuvette parameter. The controller may be configured to provide the output indicative of the cuvette parameter to the display for displaying a message to the operator indicative of the cuvette parameter. The controller may be configured to display a message indicating that the contamination level of the cuvette is equal to or above a predetermined contamination threshold or that the contamination level is below the predetermined contamination threshold. The contamination level being equal to or above the contamination threshold may indicate to the operator that an analysis of the blood sample using the cuvette cannot be performed. The contamination level being below the contamination threshold may indicate to the operator that the operator may proceed with the analysis of the blood sample using the cuvette.

In one or more example blood analyzers, the controller may provide the output indicative of the cuvette parameter to a compensation function which can compensate for the contamination level during subsequent measurements and determination of blood parameters using the cuvette.

In one or more example blood analyzers, the controller is configured to control the photometer to obtain, during the second rotation cycle, third absorbance data indicative of a separation time of red blood cells from the plasma in the sample analysis cavity of the cuvette. The controller may be configured to obtain the third absorbance data by being configured to control the photometer to measure absorbance of the blood sample in the sample analysis cavity using two or more wavelengths, such as two, three, four, five, six or more wavelengths.

In one or more example blood analyzers, the controller is configured to determine, based on the third absorbance data and the first absorbance data, a third blood parameter being, such as being indicative of, an ESR of the blood sample in the sample analysis cavity of the cuvette.

In one or more example blood analyzers, the controller is configured to provide an output indicative of the third blood parameter. The controller may be configured to provide the output indicative of the third blood parameter to the display for displaying a message to the operator indicative of the third blood parameter. The controller may be configured to control the display to display a message indicating that the ESR is higher or lower than an ESR threshold. The ESR threshold may be an ESR indicative of a normal ESR, such as an ESR range, for a healthy person.

In one or more example blood analyzers, the analyzer comprises an imaging device, such as a camera. The controller may be configured to control the imaging device to obtain, after the second rotation cycle, first image representing an image of at least a part of the blood sample in the sample analysis cavity of the cuvette.

In one or more example blood analyzers, the controller is configured to determine, based on the first image data, a fourth blood parameter being, such as being indicative of, the hematocrit level of the blood sample.

In one or more example blood analyzers, the controller is configured to provide an output indicative of the fourth blood parameter. The controller may be configured to provide the output indicative of the hematocrit level to the display for displaying a message to the operator indicative of the fourth blood parameter. In one or more example blood analyzers, the output may be an error code. The controller may be configured to present an error code upon the fourth blood parameter being above a hematocrit threshold instead of outputting erroneous results. The hematocrit threshold may for example indicate an amount of blood cells at which it is not possible to gain sufficient amount of plasma, thus leading to unwanted blood cells in the measuring eye.

In one or more example blood analyzers, the controller is configured to rotate the rotatable member at a third speed in a third rotation cycle, wherein the third speed is higher than the first speed, the second speed and the initial speed. The controller may be configured to perform the third rotation cycle after the second rotation cycle.

In one or more example blood analyzers, the controller is configured to control the photometer to obtain, during the third rotation cycle, fourth absorbance data indicative of an absorbance in the blood sample in the sample analysis cavity of the cuvette.

In one or more example blood analyzers, the controller is configured to determine, based on the fourth absorbance data, a fifth blood parameter being, such as being indicative of, a second plasma free hemoglobin level indicating fragile blood cells of the blood sample.

In one or more example blood analyzers, the photometer is configured to obtain initial absorbance data, first absorbance data, second absorbance data, third absorbance data, or fourth absorbance data by measuring absorbance using more than two wavelengths.

In one or more example blood analyzers, the controller is configured to control the photometer and any imaging device, respectively, to measure initial absorbance data, first absorbance data, second absorbance data, third absorbance data, or fourth absorbance data during a plurality of revolutions of the rotatable member.

In one or more example blood analyzers, the controller is configured to integrate absorbance data obtained by the photometer during the plurality of revolutions of the rotatable member.

A cuvette for blood analysis, and suitable to be used in the methods and for the blood analyzer defined herein, is disclosed in the following. The cuvette comprises a sampling cavity comprising a fluid inlet for taking up, such as obtaining, the blood sample, a sample analysis cavity for analyzing the blood sample, and a venting cavity.

The venting cavity is in fluid connection with the sampling cavity and the sample analysis cavity, such that the blood sample can flow from the sampling cavity to the sample analysis cavity via the venting cavity. The sampling cavity and the sample analysis cavity are not in direct fluid communication with each other. Hence, for the blood sample to move from the sampling cavity to the sample analysis cavity, the blood sample must flow through the venting cavity.

The cuvette is configured to transfer, upon a force, such as a centrifugal force, being applied to the cuvette, the blood sample from the sampling cavity to the sample analysis cavity via the venting cavity. In one or more example cuvettes, the cuvette has a first interface fluidly connecting the venting cavity with the sampling cavity. The first interface may be configured to allow the blood sample to flow through the first interface when a centrifugal force overcoming the third capillary force is applied to the cuvette. In one or more example cuvettes, the cuvette has a second interface fluidly connecting the venting cavity with the sample analysis cavity. The second interface may be configured to allow the blood sample to flow through the second interface from the venting cavity to the sample analysis cavity and may prevent a flow from the sample analysis cavity to the venting cavity. In one or more example cuvettes, the blood sample may spontaneously flow through the second interface, for example due to the first capillary force of the sample analysis cavity being higher than a second capillary force provided by the venting cavity. In one or more example cuvettes, the cuvette is absent of any means, such as capillary channels and/or siphons, configured to draw the blood sample away from the sample analysis cavity.

The blood sample introduced into the cuvette via the sampling cavity may be separated in the sample analysis cavity by further application of a centrifugal force once the blood sample has entered the sample analysis cavity. For example, red blood cells or disturbing elements may be separated out from a whole blood sample. In other words, the blood sample may be separated and analyzed in the same cavity, such as in the sample analysis cavity. The sample analysis cavity may thus act as a centrifugal cavity. In other words, the cuvette may not comprise a centrifugal cavity for separating the blood sample in addition to the sample analysis cavity. In one or more example cuvettes, the sample analysis cavity is the innermost cavity of the cuvette. Thereby, the separated body fluid is arranged in the innermost cavity of the cuvette, which reduces the risk of the separated body fluid being contaminated by coming into contact with the outside of the cuvette.

In one or more example cuvettes, the first interface and the second interface are arranged at an angle to each other. The first interface may be arranged along a first axis, such as along a longitudinal axis, of the cuvette. The second interface may be arranged along a second axis, such as along a lateral axis, of the cuvette. The first interface and the second interface may for example be arranged substantially perpendicular to each other. Substantially perpendicular may herein be seen as being arranged at an angle in the range of 80-100 degrees to each other. However, other angles may also be envisaged. The second interface may in one or more example cuvettes, be arranged perpendicular to the longitudinal direction of the cuvette, such as perpendicular to a direction of a centrifugal force to be applied to the cuvette. In other words, when the cuvette is arranged in the analyzer and a centrifugal force is applied to the cuvette, the centrifugal force may act in the longitudinal direction of the cuvette.

The sample analysis cavity is configured to provide a first capillary force, the first capillary force being higher than the second capillary force provided by the venting cavity. The first capillary force may be achieved by a height and/or a width of the sample analysis cavity being smaller than a capillary force achieved by a height and/or a width of the venting cavity. The height of the sample analysis cavity and the venting cavity may herein be seen as a distance between a first inner surface and a second inner surface of the respective cavity in a vertical direction of the cuvette, as defined in FIG. 4. By decreasing the distance between the inner surfaces of the cavity, the capillary force of the cavity may be increased. By configuring the sample analysis cavity to have a higher capillary force than the venting cavity, i.e., the first capillary force being larger than the second capillary force, a transport of the blood sample from the venting cavity to the sample analysis cavity may be enhanced, while a transport of the fluid from the sample analysis cavity to the venting cavity may be prevented. The cuvette may thus be configured to prevent the blood sample from leaving the sample analysis cavity after the centrifugal force is removed. Thereby, it can be ensured that the entire volume of the blood sample remains in the sample analysis cavity after the centrifugal force has been removed from the cuvette. The entire volume can herein be seen as at least 90%, such as 95%, 96%, 97%, 98%, 99%, or 100% of the volume of blood obtained by the sampling cavity.

The venting cavity has an opening to the exterior of the cuvette, which opening may herein be referred to as a venting opening. The venting opening may form an outlet through which air can be vented from the sample analysis cavity to the exterior of the cuvette via the venting cavity upon the sample analysis cavity being filled with the blood sample. The cuvette may be configured to transfer, when blood is introduced into, such as taken up by, the sampling cavity, air from the sampling cavity to an exterior of the cuvette via the venting cavity and/or via the sampling cavity.

The venting opening may in one or more example cuvettes be arranged at a first end of the cuvette. The venting opening may cover an entire width of the venting cavity, such that an entire side of the venting cavity may be open to the exterior of the cuvette.

In one or more example cuvettes, the venting opening is an opening through an outer side wall of the cuvette. The venting opening may extend over a part of or an entire width of the venting cavity. The opening allows air to escape from any of the cavities, such as the venting cavity, the sampling cavity and/or the sample analysis cavity, through the venting cavity to an exterior of the cuvette, when the cavity is filled with the blood sample. In one or more example cuvettes, the outlet of the venting cavity to the exterior of the cuvette is arranged at a first end of the cuvette, such as at a first longitudinal end of the cuvette.

In one or more example cuvettes, the sampling cavity has an opening through an outer side wall of the cuvette, which opening may herein be referred to as a sampling opening. The sampling opening may extend over a part of or an entire width of the sampling cavity. The sampling opening can allow air to escape from the sampling cavity when the sampling cavity takes up, such as is filled with, the blood sample. In one or more example cuvettes, the sampling opening of the sampling cavity to the exterior of the cuvette is arranged at the first end of the cuvette. The sampling opening and the venting opening may thus be arranged at the same end of the cuvette.

In one or more example cuvettes, the venting opening and/or the sampling opening extending over the entire width of the respective cavities can allow a removal of a shaping tool being used during manufacturing of the cuvette. Thereby manufacturing of the cuvette may be facilitated which can reduce a time and a cost for manufacturing the cuvette.

The sampling cavity may be configured to provide a third capillary force. The third capillary force may be higher than the second capillary force in the venting cavity. By configuring the cuvette such that the third capillary force is higher than the second capillary force, a spontaneous transport of the blood sample from the sampling cavity can be prevented. Spontaneous transport herein means a transport without application of an external force, such as a centrifugal force, to the cuvette. The higher capillary force in the sampling cavity may be achieved by the sampling cavity having a height being smaller than the height of the venting cavity. The height of the cavity may herein be seen as a distance between two parallel inner surfaces of the respective cavities. The third capillary force of the sampling cavity may be the same as or different than the first capillary force, such as the capillary force of the sample analysis cavity. Since the cuvette is configured such that a spontaneous transport of the blood from the sampling cavity is prevented, the sampling cavity may be filled with a sample in several steps without obtaining excess fluid. Thus, in case the sampling cavity has not been properly filled, more fluid may be drawn into the sampling cavity for filling up the sampling cavity. Hence, if it is noted that the inlet cavity is not completely filled with fluid, the cuvette may again be brought in contact with a fluid to be sampled such that more fluid will be drawn into the inlet cavity by capillary action in the sampling cavity. Thereby a pre-defined sample volume corresponding to the volume of the sampling cavity can always be acquired.

In one or more example cuvettes, the cuvette consists of a main body member, such as a single main body member, having inner walls defining the sampling cavity, the sample analysis cavity, and the venting cavity within the body. A single body member herein means that the cuvette is made of one integral part, for example by molding or casting. By making the cuvette as an integral part, the cuvette does not comprise any joints through which the blood may escape the cuvette during centrifugation. Thereby contamination of the outside of the cuvette and the blood analyzer can be reduced, which reduces the time needed between analyses for cleaning and preparing the analyzer for receiving another cuvette.

The sampling cavity, the sample analysis cavity and the venting cavity may be arranged in a main body member of the cuvette. The main body member of the cuvette may be made of a material having a low absorbance of radiation in wavelengths used during analysis of the blood sample. In one or more example cuvettes, the material of the cuvette may be a plastic, such as polystyrene (PS), polymethylmethacrylate (PMMA), or polycarbonate (PC).

The centrifugal force being applied to the cuvette may overcome the third capillary force holding the blood sample in the sampling cavity. The blood sample may thus leave the sampling cavity via the venting cavity and may enter the sample analysis cavity. The sample analysis cavity may be arranged offset from the sampling cavity in the longitudinal direction of the cuvette. Thereby, the centrifugal force may force the blood sample towards and into the sample analysis cavity.

The cuvette may be configured to transfer, upon the centrifugal force being applied to the cuvette, air from the sample analysis cavity to an exterior of the cuvette via the venting cavity. Upon the blood sample entering the sample analysis cavity, air in the sample analysis cavity may escape the sample analysis cavity to an exterior of the cuvette via the second interface and the venting opening, thereby ensuring a proper filling of the sample analysis cavity.

In one or more example cuvettes, the sampling cavity and the sample analysis cavity have equal volumes, such as substantially equal volumes. Thereby, a predefined volume of the blood sample may be obtained by the sampling cavity and the same volume of the fluid can be analyzed in the sample analysis cavity.

The volume of the sampling cavity may be in the range of 10-100 microliters (μL), or 20-60 microliters (μL), such as in the range of 30-50 μL, such as in the range of 30-40 μL, such as in the range of 30-35 μL, such as 32 μL. The volume of the sample analysis cavity may be in the range of 10-100 microliters (μL), or 20-60 microliters (μL), such as in the range of 30-50 μL, such as in the range of 30-40 μL, such as in the range of 30-35 μL, such as 32 μL.

In one or more example cuvettes, the sample analysis cavity has a substantially uniform elongated shape extending in a first direction between the first end and an opposing second end of the cuvette. The first end and the second end of the cuvette may be arranged at opposing longitudinal ends of the cuvette. The first direction may be parallel to an intended direction of the centrifugal force to be applied to the cuvette, such as to the direction of the centrifugal force applied to the cuvette when the cuvette is analyzed using the blood analyzer configured to receive the cuvette.

Figure 4:
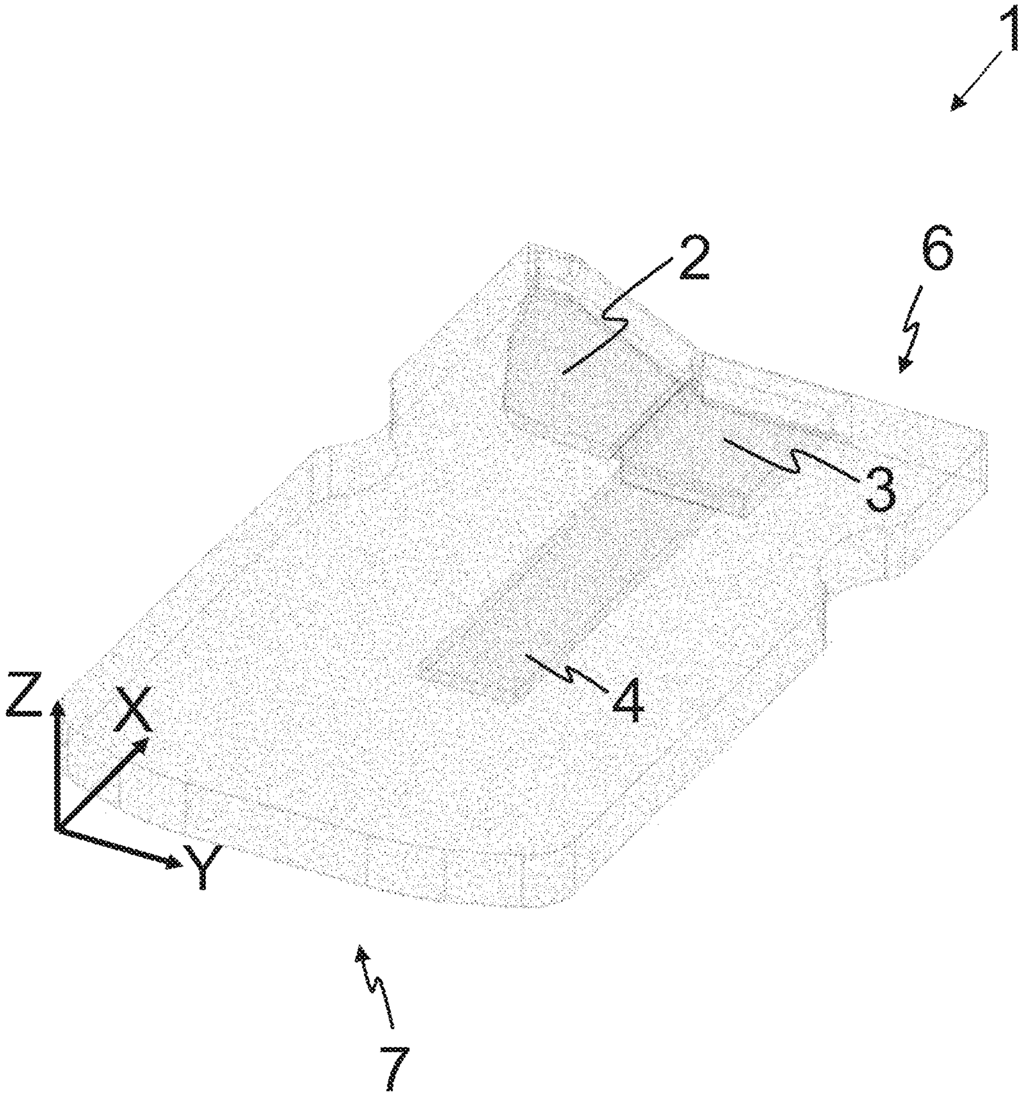
FIG. 4 illustrates a perspective view of an example cuvette according to this disclosure.

In one or more example cuvettes, an overall length of the cuvette, such as an extension in the longitudinal direction of the cuvette as defined in FIG. 4, may be in the range of 30-50 mm, or 36-44 mm, such as in the range of 38-42 mm, such as in the range of 39-40 mm. The overall length may be measured from the tip of the first longitudinal end of the cuvette to the second longitudinal end of the cuvette.

In one or more example cuvettes, an overall width of the cuvette, such as an extension in a lateral direction of the cuvette as defined in FIG. 4, may be in the range of 15-28 mm, or 18-24 mm, such as in the range of 19-23 mm, such as in the range of 20-22 mm. In one or more example methods, the width of the cuvette may be 21 mm.

In one or more example cuvettes, an overall width of the cuvette, such as an extension in a vertical direction of the cuvette as defined in FIG. 4, may be in the range of 1.9-2.4 mm, such as in the range of 2.0-2.3 mm, such as in the range of 2.1-2.2 mm.

In one or more example cuvettes, the sample analysis cavity may have a length, such as an extension in the longitudinal direction of the cuvette as defined in FIG. 4, in the range of 10-20 mm, such as 10 mm, 11 mm, 12 mm, 13 mm, 14 mm, 15 mm, 16 mm, 17 mm, 18 mm, 19 mm or 20 mm, and/or any ranges constrained by the dimensions discussed in this paragraph.

In one or more example cuvettes, the sample analysis cavity may have a width, such as an extension in a lateral direction of the cuvette as defined in FIG. 4, in the range of 2-7 mm, such as 2 mm, 3 mm, 4 mm, 5 mm, 6 mm or 7 mm, and/or any ranges constrained by the dimensions discussed in this paragraph.

In one or more example cuvettes, the sample analysis cavity may have a height, such as an extension in a vertical direction of the cuvette as defined in FIG. 4, in the range of 0.2-0.7 mm, such as 0.2 mm, 0.3 mm, 0.4 mm, 0.5 mm, 0.6 mm or 0.7 mm, and/or any ranges constrained by the dimensions discussed in this paragraph. In one or more example cuvettes, the height of the sample analysis cavity may be 0.5 mm, such as 500 μm.

In one or more example cuvettes, the sampling cavity may have a length, such as an average length, in the range of 5-15 mm, such as 5 mm, 6 mm, 7 mm, 8 mm, 9 mm, 10 mm, 11 mm, 12 mm, 13 mm, 14 mm or 15 mm, and/or any ranges constrained by the dimensions discussed in this paragraph.

In one or more example cuvettes, the sampling cavity may have a width, such as an average width, in the range of 5-15 mm, such as 5 mm, 6 mm, 7 mm, 8 mm, 9 mm, 10 mm, 11 mm, 12 mm, 13 mm, 14 mm or 15 mm, and/or any ranges constrained by the dimensions discussed in this paragraph.

In one or more example cuvettes, the sampling cavity may have a height, such as an extension in a vertical direction of the cuvette as defined in FIG. 4, in the range of 0.2-0.7 mm, such as 0.2 mm, 0.3 mm, 0.4 mm, 0.5 mm, 0.6 mm or 0.7 mm, and/or any ranges constrained by the dimensions discussed in this paragraph. In one or more example cuvettes, the height of the sampling cavity may be in the range of 500-650 μm, such as 575 μm.

In one or more example cuvettes, the venting cavity may have a length in the range of 5-10 mm, such as 5 mm, 6 mm, 7 mm, 8 mm, 9 mm or 10 mm, and/or any ranges constrained by the dimensions discussed in this paragraph.

In one or more example cuvettes, the venting cavity may have a width in the range of 3-8 mm, such as 3 mm, 4 mm, 5 mm, 6 mm, 7 mm or 8 mm, and/or any ranges constrained by the dimensions discussed in this paragraph.

In one or more example cuvettes, the venting cavity may have a height, such as an extension in a vertical direction of the cuvette as defined in FIG. 4, in the range of 0.4-2 mm, such as 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, or 2.0 mm, and/or any ranges constrained by the dimensions discussed in this paragraph. In one or more example cuvettes, the height of the venting cavity may be 1 mm, such as 1000 μm.

In one or more example cuvettes, the body member comprises a tip. The sampling cavity may be arranged at the tip of the body member, such that the inlet of the sampling cavity is arranged at the tip of the cuvette. By arranging the inlet at the tip of the cuvette filing of the sampling cavity with a blood sample can be facilitated, since the tip allows a precise positioning of the inlet of the sampling cavity at a blood sample to be taken up.

In one or more example cuvettes, the sampling cavity, such as an inner surface of the sampling cavity, is configured to slope towards the sample analysis cavity. By providing the sampling cavity with a slope the transportation of the blood sample from the sampling cavity to the sample analysis cavity may be improved. The sampling cavity may be configured to slope outwards towards the opening of the further facilitates removal of a shaping tool after shaping of the cuvette.

In one or more example cuvettes, the cuvette, such as the sample analysis cavity of the cuvette, is free of reagents. When the cuvette is free of reagents, the analysis of the blood sample, such as the blood sample, may be done by measuring directly at the hemoglobin (Hb) derivates comprised in the body. For blood, the hemoglobin derivatives may be for example reduced hemoglobin (Hb), such as deoxyhemoglobin (reduced), oxyhemoglobin (HbO2), methemoglobin (met-Hb), carboxyhemoglobin (HbCO) or other types of hemoglobin. Making the cuvette free of reagents reduced the cost of manufacturing the cuvette and also reduced the time it takes to manufacture the cuvette.

In one or more example cuvettes, the walls of the sampling cavity are coated with a wetting agent. The wetting agent may aid in taking up blood samples in the sampling cavity.

In one or more example cuvettes, the sample analysis cavity may comprise a reagent configured to react with the blood sample. The reagent may be arranged on an inner surface of the sample analysis cavity, such that it comes in contact with the blood sample when the blood sample enters the sample analysis cavity. The reagent may be applied to the sample analysis cavity during manufacturing of the cuvette. Different reagents may be provided in the cavity depending on the analysis that is to be performed, thereby enabling the cuvette to be adapted for analysis of different biological parameters of blood. The reagent may cause the different hemoglobin derivates to react into the same derivate, thereby reducing interference at the different wavelengths which may facilitate the analysis procedure of the blood sample.

In one or more example cuvettes, the cuvette may comprise a unique identifier for identifying each respective cuvette. The unique identifier may be a visual identifier, such as a barcode or a QR-code, or a digital identifier, such as a Radio Frequency Identification (RFID) tag. The unique identifier may be used to identify the cuvette being used for a specific blood sample and/or analysis. In one or more example cuvettes, the identifier may be identified by the blood analyzer and measurements from the blood analyzer may be automatically stored with the unique identifier of the cuvette.

The cuvette may be a single-use cuvette, e.g. configured for one time use, such as may be disposable and is to be thrown away after having been used once for analysis.

The cuvette may be manufactured by conventional means, e.g. as disclosed in WO 2007/008137 A1.

In the following, the method for analyzing a blood sample, the analyzer for analyzing a blood sample and the cuvette for analyzing a blood sample of the current disclosure will be described in further detail with reference to the figures. The figures are schematic in nature and simplified for clarity, and they merely show details which aid understanding the disclosure, while other details have been left out. Throughout, the same reference numerals are used for identical or corresponding parts.

FIG. 1 illustrates a method 100 for analyzing a blood sample. The method may be performed using a blood analyzer. A blood analyzer may herein be seen as an analysis apparatus for analysing blood.

The method comprises arranging S102 a cuvette comprising a sampling cavity and a sample analysis cavity on a rotatable member. The sampling cavity comprises a blood sample to be analyzed.

In one or more example methods, the method may comprise rotating S104 the rotatable member at an initial speed in an initial rotation cycle insufficient for transfer of the blood sample from the sampling cavity to the sample analysis cavity. The initial speed may create an initial centrifugal force acting on the blood sample during the initial rotation cycle that is below a capillary force acting on the blood sample in the sampling cavity. In other words, the initial speed may be insufficient for transferring blood from the sampling cavity to the sample analysis cavity. Thereby, the blood sample will be held in the sampling cavity during the initial rotation cycle. The sample analysis cavity will thus remain empty, wherein empty herein means not comprising any blood, which allows an initial measurement to be performed on the empty sample analysis cavity of the cuvette to detect any contamination or damages to the cuvette which could affect the analysis results of the blood sample. In one or more example methods, the initial rotation cycle is performed prior to a first rotation cycle.

In one or more example methods, the method may comprise obtaining S106, using the photometer and during the initial rotation cycle, initial absorbance data indicative of an absorbance in or through the sample analysis cavity of the cuvette. Since the blood sample is held in the sampling cavity during the initial rotation cycle, the initial absorbance data may be absorbance data indicative of an absorbance through the empty sample analysis cavity.

In one or more example methods, the method may comprise determining S108, based on the initial absorbance data, a cuvette parameter. The cuvette parameter may be, such as may be indicative of, a contamination level associated with the cuvette, absorbance data of the empty cuvette, and a presence of a cuvette in the receptacle of the rotatable member. The contamination level associated with the cuvette may comprise scratches on the surface of the cuvette, discoloration of the cuvette, contamination of the cuvette, and/or any other imperfections of the cuvette, in the area of the sample analysis cavity of the cuvette. The contamination may for example be caused by fingerprints added to the area of the sample analysis cavity due to incorrect handling of the cuvette by an operator.

In one or more example methods, the method comprises providing S109 an output indicative of the cuvette parameter. In one or more example methods, providing S109 the output may comprise displaying S109A a message to the operator indicative of the cuvette parameter. The message may for example indicate that the contamination level of the cuvette is equal to or above a predetermined contamination threshold or that the contamination level is below the predetermined contamination threshold. The contamination level being equal to or above the contamination threshold may indicate to the operator that an analysis of the blood sample using the cuvette cannot be performed. The contamination level being below the contamination threshold may indicate to the operator that the operator may proceed with the analysis of the blood sample using the cuvette.

In one or more example methods, providing S109 the output may comprise providing S109B the cuvette parameter to a compensation function which can compensate for the contamination level and/or the absorbance data of the empty cuvette, during subsequent measurements and determination of blood parameters using the cuvette.

The method comprises rotating S110 the rotatable member at a first speed in a first rotation cycle for transfer of the blood sample from the sampling cavity to the sample analysis cavity. The first speed may be configured to create a first centrifugal force that is greater than a third capillary force produced by the sampling cavity of the cuvette. The first centrifugal force transfers the blood sample from the sampling cavity to the sample analysis cavity. In one or more example methods, the first rotation cycle is performed after the initial rotation cycle.

In one or more example methods, the method may comprise obtaining S112, using the photometer and during the first rotation cycle, a first absorbance data indicative of an absorbance in the blood sample in the sample analysis cavity of the cuvette.

In one or more example methods, the method may comprise determining S113, based on the first absorbance data, a filling parameter indicative of a blood level, such as indicative of a fill level, such as indicative of the amount of blood, in the sample analysis cavity of the cuvette. The filling parameter may, in one or more example methods, be indicative of one or more of the sample analysis cavity being underfilled, the sample analysis cavity being incorrectly filled, and the sample analysis cavity being correctly filled. In one or more example methods, the sample analysis cavity may be determined to be underfilled when the first absorbance data is below a first blood level threshold. A too low blood level, such as an underfilled cuvette, may cause the absorbance data to be lower than when the sample analysis cavity is correctly filled. The sample analysis cavity being incorrectly filled can herein be seen as not being filled with blood, such as being filled with a fluid other than blood.

In one or more example methods, the method comprises providing S113A an output indicative of the filling parameter, such as indicative of the amount of blood, in the sample analysis cavity of the cuvette. In one or more example methods, the output may indicate that a further analysis of the blood sample is not possible, such as when the filling parameter indicates that the cuvette is underfilled, and/or incorrectly filled. In one or more example methods, the output may indicate that a further analysis of the blood sample is possible, such as when the filling parameter indicates that the cuvette is correctly filled. In one or more example methods, the output may be a signal preventing a further analysis of the blood sample, such as when the filling parameter indicates that the cuvette is underfilled and/or incorrectly filled. In one or more example methods, the output may be a signal allowing a further analysis of the blood sample, such as when the filling parameter indicates that the cuvette is correctly filled.

In one or more example methods, the method may comprise determining S114, based on the first absorbance data, a first blood parameter being, such as being indicative of, a total hemoglobin level of the blood sample.

The method comprises rotating S116 the rotatable member at a second speed in a second rotation cycle for separating blood parts from plasma in the blood sample. The second rotation cycle may be performed after the first rotation cycle.

The method comprises obtaining S118, using a photometer, during or after the second rotation cycle, second absorbance data. The second absorbance data being indicative of absorbance in the plasma.

The method comprises determining S119, based on the second absorbance data, a second blood parameter. The second blood parameter being, such as being indicative of, a plasma free hemoglobin level of the blood sample.

The method comprises providing S120 an output indicative of the second blood parameter.

In one or more example methods, the method may comprise obtaining S121, using the photometer, during the second rotation cycle, third absorbance data indicative of a separation time of red blood cells from the plasma.

In one or more example methods, the method may comprise determining S122, based on the third absorbance data and the first absorbance data, a third blood parameter. The third blood parameter being, such as being indicative of, an erythrocyte sedimentation rate of the blood sample.

In one or more example methods, the method may comprise providing S123 an output indicative of the third blood parameter.

In one or more example methods, the method may comprise obtaining S124, using an imaging device, after the second rotation cycle, first image data representing an image of at least a part of the blood sample in the sample analysis cavity.

In one or more example methods, the method may comprise determining S126, based on the first image data, a fourth blood parameter being, such as being indicative of, the hematocrit level of the blood sample.

In one or more example methods, the method may comprise providing S128 an output indicative of the fourth blood parameter.

In one or more example methods, the method may comprise after the second rotation cycle, rotating S130 the rotatable member at a third speed in a third rotation cycle. In one or more example methods, the third speed is higher than the first speed, the second speed and the initial speed. In one or more example methods, the third speed may be equal to the second speed. In one or more example methods, the third rotation cycle may be longer than the second rotation cycle, for inducing hemolysis in the blood sample. In other words, hemolysis may be induced to the blood sample during the third rotation cycle by centrifuging the blood sample at a higher speed or for a longer time than the second rotation cycle.

In one or more example methods, the method may comprise obtaining S132, using the photometer and during the third rotation cycle, fourth absorbance data indicative of an absorbance in the blood sample in the sample analysis cavity of the cuvette.

In one or more example methods, the method may comprise determining S134, based on the fourth absorbance data, a fifth blood parameter. The fifth blood parameter may be a second plasma free hemoglobin level indicating fragile blood cells of the blood sample. By comparing the second plasma free hemoglobin level with the first plasma free hemoglobin level a level of fragile blood cells in the blood sample can be determined.

In one or more example methods, the method may comprise providing S136 an output indicative of the fifth blood parameter, such as displaying information indicative of the fifth blood parameter.

Figure 2:
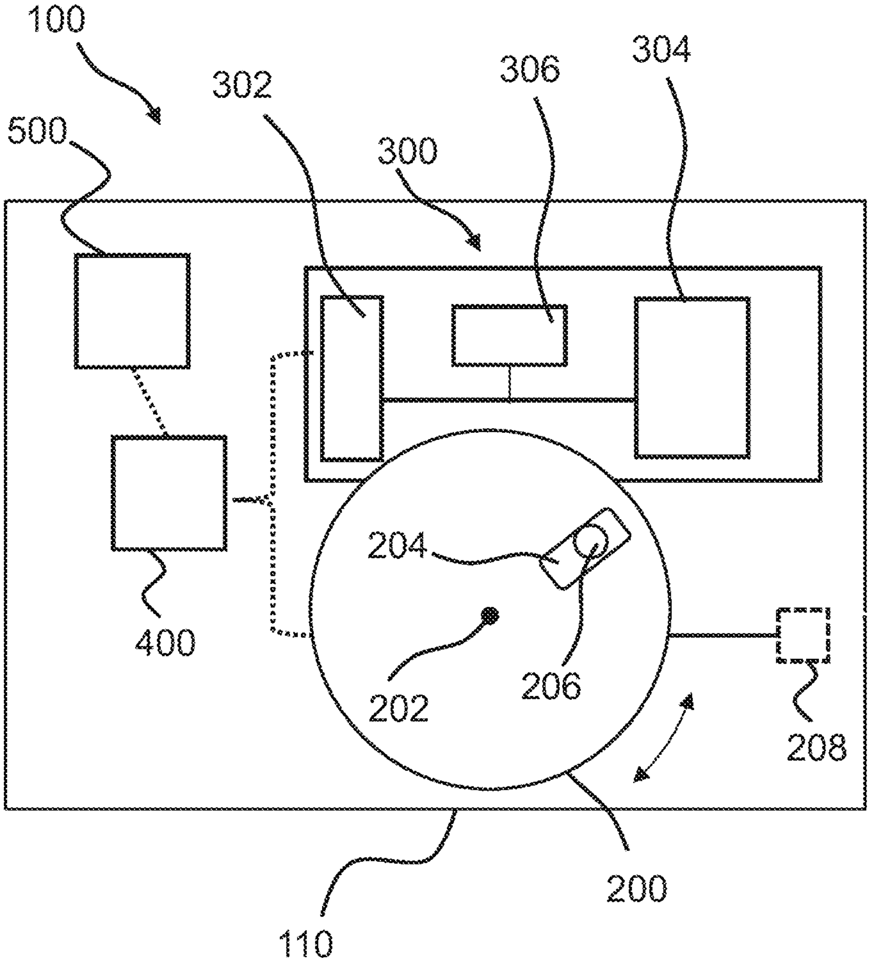
FIG. 2 illustrates an analyzer for analyzing a blood sample according to this disclosure.

FIG. 2 illustrates a schematic of an example blood analyzer 100 according to this disclosure. The blood analyzer 100 can comprise a housing 110, which can accommodate any and/or all of the parts of the blood analyzer 100 discussed herein, such as the rotatable member, the photometer, the controller, the display and/or the drive unit.

The blood analyzer 100 comprises a rotatable member 200. The rotatable member 200 is rotatably arranged in the housing 110. The rotatable member 200 may be rotatable arranged around a rotational axis 202. The rotatable member comprises a receptacle 204 for receiving a cuvette. The cuvette comprises a sampling cavity and a sample analysis cavity. When the cuvette is arranged on the rotatable member, the sampling cavity of the cuvette is intended to comprise a blood sample to be analyzed, whereas the sample analysis cavity is intended to be empty. Empty herein means that the sample analysis cavity does not comprise any blood sample but may comprise air. The rotatable member 200 may be a circular member, such as a disc. The receptacle 204 can comprise a measuring eye 206, such as an opening, for allowing light to pass through the rotatable member 200. The measuring eye 206 may be arranged in the receptacle 204 so that the measuring eye 206, in at least a first angular position of the rotatable member 200, overlaps with the sample analysis cavity of the cuvette, when the cuvette is arranged in the receptacle 204. The measuring eye 206 can be arranged at a distance r from the rotational axis 202 on the rotatable member 200. The blood analyzer 100 can comprise a drive unit 208, such as an electric motor, for driving, such as rotating, the rotatable member 200.

The blood analyzer 100 comprises a photometer 300. The photometer 300 is configured to obtain, such as measure, absorbance data associated with the sample analysis cavity and/or the blood sample of the cuvette. The photometer 300 can be a multi-wavelength photometer. The photometer 300 can comprise a light source 302 for emitting light at respective wavelengths and an optical sensor 304, such as a photo diode, for measuring how much light is absorbed by an object located between the light source 302 and the optical sensor 304.

The blood analyzer 100 can comprise a display 500 configured to visually provide information to an operator of the blood analyzer 100, such as for visually displaying information indicative of the cuvette parameter, the first blood parameter, the second blood parameter, the third blood parameter, the fourth blood parameter, and/or the fifth blood parameter.

The blood analyzer 100 can comprise a display 500 for displaying, such as visually providing, information to an operator of the blood analyzer 100.

The blood analyzer 400 can comprise an imaging device 306, such as a camera, for taking images associated with the sample analysis cavity and/or the blood sample of the cuvette.

The blood analyzer can comprise a controller 400. The controller 400 can be configured to control the photometer 300, any imaging device 306, the rotatable member 200, the drive unit 208 and/or the display 500. The controller 400 may be configured to perform any one of the of the operations disclosed in FIG. 1*a*-1*d* (such as any one or more of S102, S104, S106, S108, S110, S112, S114, S116, S118, S119, S120, S121, S122, S123, S124, S126, S128, S130, S132, S134).

The controller 400 may be configured to control the drive unit 208 to control the speed of the rotatable member 200.

The controller 400 can be configured to rotate the rotatable member 200 at a first speed in a first rotation cycle for transferring the blood sample from the sampling cavity to the sample analysis cavity.

The controller 400 can be configured to rotate the rotatable member 200 at a second speed in a second rotation cycle after the first rotation cycle for separating blood parts from plasma in the blood sample.

The controller 400 can be configured to control the photometer 300 to obtain, during the second rotation cycle, second absorbance data indicative of absorbance in the plasma of the separated blood sample.

The controller 400 can be configured to determine, based on the second absorbance data, a second blood parameter being, such as being indicative of, a plasma free hemoglobin level of the blood sample.

The controller 400 can be configured to provide an output, such as to the display 500, indicative of the second blood parameter.

The controller 400 can be configured to, prior to the first rotation cycle, rotate the rotatable member 200 at an initial speed in an initial rotation cycle. The initial speed is insufficient for transfer of the blood sample from the sampling cavity to the sample analysis cavity.

The controller 400 can be configured to control the photometer 300 to obtain, during the initial rotation cycle, initial absorbance data indicative of an absorbance in the sample analysis cavity of the cuvette.

The controller 400 can be configured to determine, based on the initial absorbance data, a cuvette parameter being, such as being indicative of, a contamination level associated with the cuvette.

The controller 400 can be configured to provide, such as to the display 500, an output indicative of the cuvette parameter.

The controller 400 can be configured to control the photometer 300 to obtain, during the first rotation cycle, first absorbance data indicative of an absorbance in the blood sample in the sample analysis cavity of the cuvette.

The controller 400 can be configured to determine, based on the first absorbance data, a first blood parameter being, such as being indicative of, total hemoglobin level of the blood sample, and The controller 400 can be configured to provide, such as to the display 500, an output indicative of the first blood parameter.

The controller 400 can be configured to control the photometer 300 to obtain, during the second rotation cycle, third absorbance data indicative of a separation time of red blood cells from the plasma in the sample analysis cavity of the cuvette.

The controller 400 can be configured to determine, based on the third absorbance data and the first absorbance data, a third blood parameter being, such as being indicative of, an erythrocyte sedimentation rate of the blood sample in the sample analysis cavity of the cuvette.

The controller 400 can be configured to provide, such as to the display 500, an output indicative of the third blood parameter.

The controller 400 can be configured to control the imaging device 306 to obtain, after the second rotation cycle, first image data representing an image of at least a part of the blood sample in the sample analysis cavity of the cuvette.

The controller 400 can be configured to determine, based on the first image data, a fourth blood parameter being, such as being indicative of, the hematocrit level of the blood sample.

The controller 400 can be configured to provide, such as to the display, an output indicative of the fourth blood parameter The controller 400 can be configured to, after the second rotation cycle, rotate the rotatable member 200 at a third speed in a third rotation cycle, wherein the third speed is higher than the first speed, the second speed and the initial speed.

The controller 400 can be configured to control the photometer 300 to obtain, during the third rotation cycle, fourth absorbance data indicative of an absorbance in the blood sample in the sample analysis cavity of the cuvette.

The controller 400 can be configured to determine, based on the fourth absorbance data, a fifth blood parameter being, such as being indicative of, a second plasma free hemoglobin level indicating fragile blood cells of the blood sample.

The controller 400 can be configured to control the photometer and any imaging device, respectively, to measure initial absorbance data, first absorbance data, second absorbance data, third absorbance data, image data, or fourth absorbance data during a plurality of revolutions of the rotatable member 200.

The controller 400 can be configured to integrate absorbance data obtained by the photometer 300 during the plurality of revolutions of the rotatable member 200.

Figure 3:
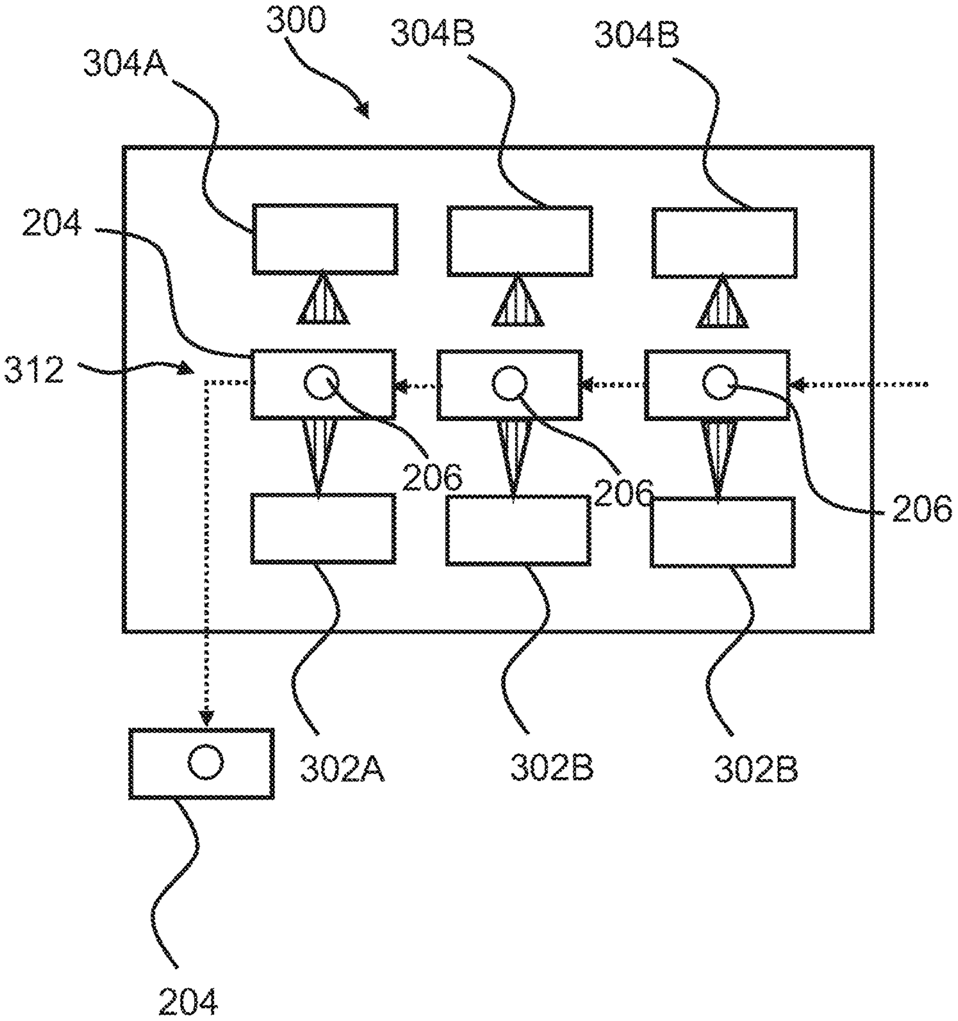
FIG. 3 illustrates a photometer for analyzing a blood sample according to this disclosure.

FIG. 3 illustrates a schematic of an example photometer 300 according to this disclosure. The photometer 300 can comprise a plurality of light sources 302, such as light sources 302A, 302B, 302C, and a plurality of optical sensors 304, such as optical sensors 304A, 304B, 304C. The light sources 302A, 302B, 302C and the corresponding optical sensors 304A, 304B, 304C may be arranged on opposite sides of the rotatable member 200, such that the light emitted from the respective light source 302A, 302B, 302C passes through the measuring eye 202 in the rotatable member 200, and the cuvette arranged in the receptacle 204 of the rotatable member 200 before it reaches the corresponding optical sensor 304A, 304B, 304C. In other words, the plurality of light sources 302A, 302B, 302C may be arranged on a first side of the rotatable member 200 and the one or more optical sensors 304A, 304B, 304C may be arranged on a second side of the rotatable member 200. The first side of the rotatable member 200 and the second side of the rotatable member 200 may be opposite sides of the rotatable member 200. In one or more example blood analyzers, the light sources 302A, 302B, 302C can be LEDs. Each light source 302A, 302B, 302C can be configured to emit light at a different wavelength. The photometer 300 can be configured to obtain the initial absorbance data, the first absorbance data, the second absorbance data, the third absorbance data, and/or the fourth absorbance data by measuring absorbance using more than two wavelengths.

FIG. 4 illustrates a perspective view of the cuvette 1 according to one or more examples of the current disclosure. The cuvette 1 comprises the sampling cavity 2, the venting cavity 3 and the sample analysis cavity 4. Throughout this document, the cuvette will be described in relation to the coordinate system disclosed in FIG. 4, where the X-axis defines a longitudinal direction spanning a length of the cuvette 1 (such as between a first longitudinal end 6 and a second longitudinal end 7 of the cuvette 1), the Y-axis defines a lateral direction spanning a width of the cuvette 1 and the Z-axis defines a vertical direction spanning a height of the cuvette 1. A main plane of the cuvette 1 as discussed herein is a plane extending in the longitudinal and lateral direction of the cuvette 1. A plane perpendicular to the main plane may herein be one or more of a plane extending in the longitudinal direction and the vertical direction of the cuvette 1 and a plane extending in the lateral direction and the vertical direction of the cuvette 1. The cuvette 1 may have a larger extension in the longitudinal and the lateral direction than in the vertical direction and may thus be referred to as a having a flat shape or as being a flat cuvette.

Figure 5:
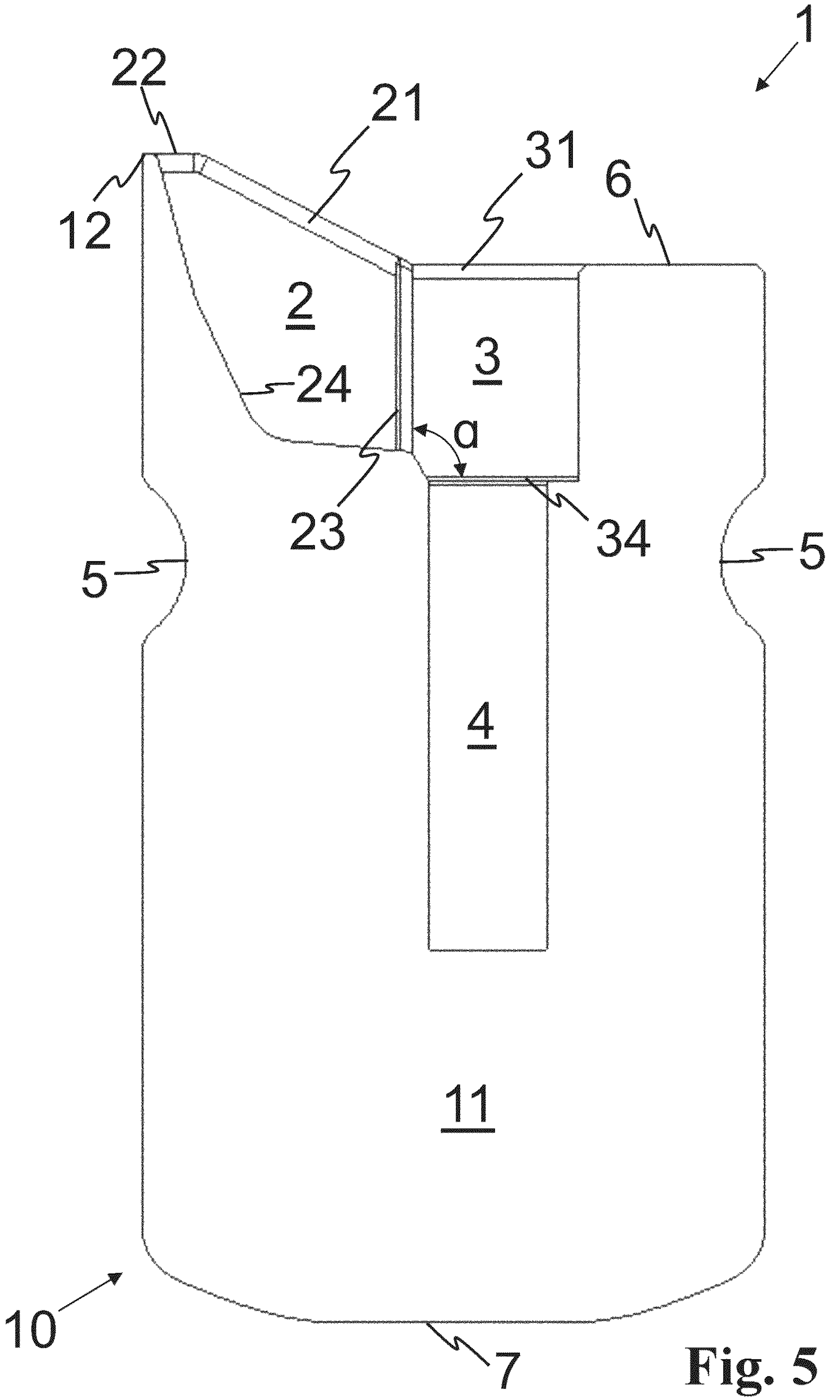
FIG. 5 illustrates a schematic of an example cuvette as disclosed herein.

FIG. 5 illustrates a cuvette 1 according to one or more examples of the current disclosure. The cuvette 1 comprises the sampling cavity 2, the sample analysis cavity 4 and the venting cavity 3. The sampling cavity 2 comprises a fluid inlet 22 for collecting a blood sample. The cuvette 1 has a main body member 10, which comprises a base portion 11. The base portion 11 may be solid and may be configured to be touched by an operator during handling of the cuvette without causing any interference with the results of the analysis of the blood. In one or more example cuvettes, the base portion 11 of the main body member 10 may have a different surface texture than the main body member 10 in area of the sampling cavity 2 and/or the sample analysis cavity 4. Providing the base portion 11 with a different surface texture can provide the operator of the cuvette a visual indication of the areas that can be touched without interfering with the analysis result. The main body member 10 may comprise mounting elements 5 that maybe configured to fit a cuvette holder in an analysis apparatus. The mounting elements 5 may be arranged such that the cuvette 1 can only be positioned in one way in the analysis apparatus. In the example cuvette 1 shown in FIG. 5, the mounting elements 5 may be shaped as indentation in the main body member 10 of the cuvette 1.

The sampling cavity 2, the sample analysis cavity 4 and the venting cavity 3 are arranged in, such as may be formed in, the main body member 10 of the cuvette 1. The cuvette 1 may consist of a single main body member 10, such as an integral part, having inner walls defining the sampling cavity 2, the sample analysis cavity 4, and the venting cavity 3 within the main body member 10. The main body member 10 of the cuvette 1 may be made of a material having a low absorbance of radiation in wavelengths used during analysis of the blood sample. The main body member 10 may be made out of plastic, such as polystyrene (PS), polymethylmethacrylate (PMMA), or polycarbonate (PC).

The venting cavity 3 is in fluid connection with the sampling cavity 2 and the sample analysis cavity 4, such that blood can flow from the sampling cavity 2 to the sample analysis cavity 4 via the venting cavity 3. The venting cavity 3 may be fluidly connected with the sampling cavity 2 via a first interface 23. The first interface 23 may be arranged along a longitudinal axis of the cuvette 1. The venting cavity 3 may be fluidly connected with the sample analysis cavity 4 via a second interface 34. The second interface 34 may be arranged along a lateral axis of the cuvette 1. The sampling cavity 2 and the sample analysis cavity 4 are not in direct fluid communication with each other. Hence, for the blood sample to move from the sampling cavity 2 to the sample analysis cavity 4, the blood sample must flow through the venting cavity 3, such as via the first interface 23 and the second interface 34.

The sample analysis cavity 4 is configured to provide a first capillary force, the first capillary force being higher than a second capillary force provided by the venting cavity 3. This may be achieved by the height of the sample analysis cavity 4 being smaller than the height of the venting cavity 3. The second interface 34 may be configured to allow the blood sample to flow through the second interface 34 from the venting cavity to the sample analysis cavity and prevent a flow of the blood sample from the sample analysis cavity 4 to the venting cavity 3. This ensures that the entire volume of the blood sample enters and remains in the sample analysis cavity 4.

The first interface 23 and the second interface 34 may be arranged at an angle a to each other. The first interface 23 and the second interface 34 may for example be arranged substantially perpendicular to each other.

The sampling cavity 2 is configured to provide a third capillary force, wherein the third capillary force is higher than the second capillary force. The third capillary force being higher than the second capillary force prevents spontaneous transport of the blood sample from the sampling cavity 2 to the venting cavity 3. This may be achieved by the height of the sampling cavity 2 being smaller than the height of the venting cavity 3. The third capillary force may be the same as or different than the first capillary force. The first interface 23 may be configured to allow the blood sample to flow through the first interface 23 when a centrifugal force overcoming the third capillary force is applied to the cuvette 1. The cuvette 1 may thus be configured to transfer, upon a centrifugal force being applied to the cuvette 1, the blood sample from the sampling cavity 2 to the sample analysis cavity 4 via the venting cavity 3.

The blood sample introduced into the cuvette 1 via the sampling cavity 2 may be separated in the sample analysis cavity 4 by further application of a centrifugal force, once the blood sample has entered the sample analysis cavity 4.

The venting cavity 3 has an outlet 31 to the exterior of the cuvette 1. The outlet 31 of the venting cavity 3 may be arranged at a first end 6, such as a first longitudinal end, of the cuvette 1. The outlet 31 may be an opening through a first outer side wall at the first end 6 of the cuvette 1, said opening extending over an entire width of the venting cavity 3. Thereby, an entire side of the venting cavity 3 may be open to the exterior of the cuvette 1. The outlet 31 is configured to allow air to be vented from the sample analysis cavity 4 to the exterior of the cuvette 1 via the venting cavity 3 upon the sample analysis cavity 4 being filled with the blood sample. The outlet 31 covering the entire width of the venting cavity 3 also allows a shaping tool to be removed from the main body member 10 after manufacturing of the cuvette 1.

The sampling cavity 2 has an opening 21 through the first outer side wall at the first end 6 of the cuvette 1. The opening 21 extends over the entire width of the sampling cavity 2. The opening 21 in the sampling cavity 2 can allow air to escape from the sampling cavity when the sampling cavity 2 takes up, such as is filled with, the blood sample. The opening 21 can further allow a removal of the shaping tool used during manufacturing of the cuvette 1. The opening 21 of the sampling cavity 2 can be arranged at the same end of the cuvette 1 as the outlet 31. The main body member 10 may comprise a tip 12. The tip 12 may be arranged at the first end 6. The side wall at the first end 6 may comprise a bend forming the tip 12. The sampling cavity 2 may be arranged at the tip 12 of the main body member 10, such that an inlet 22 of the sampling cavity 2 is arranged at the tip 12 of the cuvette 1. By arranging the inlet 22 at the tip 12 of the cuvette 1, a filing of the sampling cavity with a blood sample can be facilitated, since the tip 12 allows a precise positioning of the inlet 22 at a blood sample to be taken up. When the tip 12 is dipped into a blood sample the capillary force of the sampling cavity 2 will cause the blood to be drawn into the sampling cavity 2 via the inlet 22. The inlet 22 may be a section of the opening 21 arranged at the tip 2 of the cuvette 1. The sampling cavity 2, such as an inner surface 24 of the sampling cavity 2, may be configured to slope towards the sample analysis cavity 4. By providing the sampling cavity 2 with a sloped inner surface 24, the transportation of the blood sample from the sampling cavity 2 to the sample analysis cavity 4 may be improved. The sampling cavity 2, such as the inner surface 24, may be configured to slope outwards towards the opening 21. Thereby, the removal of the shaping tool after shaping of the cuvette 1 may be facilitated.

The sample analysis cavity 4 may have a substantially uniform elongated shape extending in a first direction from the first end 6 of the cuvette 1 to an opposing second end 7 of the cuvette 1. The first end 6 and the second end 7 of the cuvette may be arranged at opposing longitudinal ends of the cuvette 1. The first direction may be parallel to an intended direction of the centrifugal force to be applied to the cuvette, such as to the direction of the centrifugal force applied to the cuvette when the cuvette is analyzed using an analysis apparatus configured to receive the cuvette 1.

In one or more example cuvettes, the sample analysis cavity 4 may be offset from the sampling cavity 2 in the longitudinal direction of the cuvette 1. In one or more example cuvettes, the sample analysis cavity 4 may be offset from the sampling cavity 2 in the lateral direction of the cuvette 1. In one or more example cuvettes, the sample analysis cavity 4 may be offset from the sampling cavity 2 in the longitudinal direction of the cuvette 1 and in the lateral direction of the cuvette 1.

Figure 6:
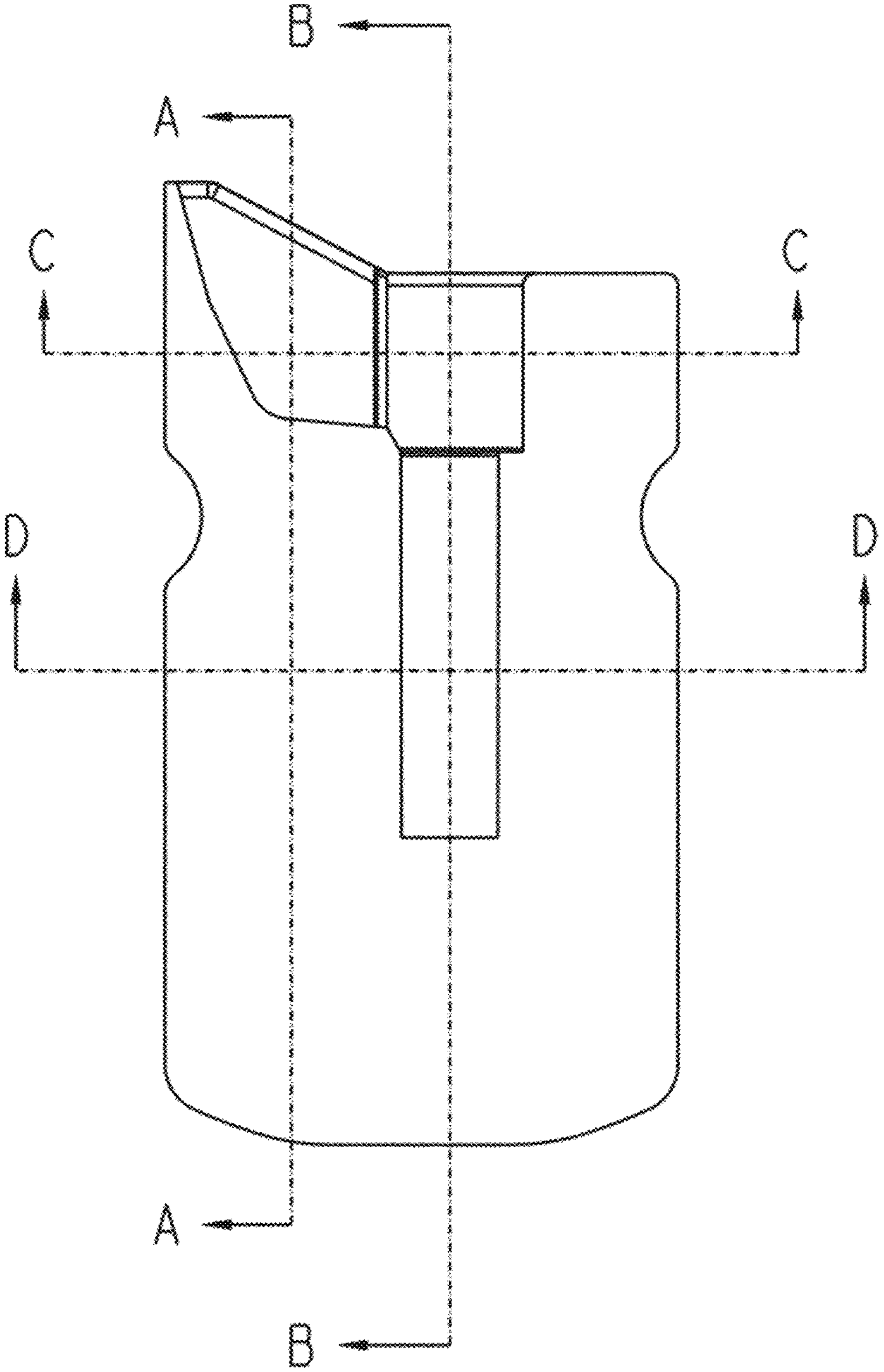
FIG. 6 illustrates a schematic of an example cuvette comprising cut lines indicating section views of the example cuvette as disclosed herein.

FIG. 6 illustrates a position of a first cutting plane A-A, a second cutting plane B-B, a third cutting plane C-C and a fourth cutting plane D-D used for the section views in FIGS. 7-10. The cutting plane A-A extends in a longitudinal direction of the cuvette through the sampling cavity 2. The section view in the cutting plane A-A will be further described with reference to FIGS. 7A and 7B. The cutting plane B-B extends in a longitudinal direction of the cuvette through the venting cavity 3 and the sample analysis cavity 4. The section view in the cutting plane A-A will be further described with reference to FIGS. 8A and 8B. The cutting plane C-C extends in a lateral direction of the cuvette 1 through the venting cavity 3 and the sampling cavity 2. The section view in the cutting plane C-C will be further described with reference to FIG. 9. The cutting plane D-D extends in a lateral direction of the cuvette 1 through the sample analysis cavity 4. The section view in the cutting plane D-D will be further described with reference to FIG. 10.

Figure 7A:
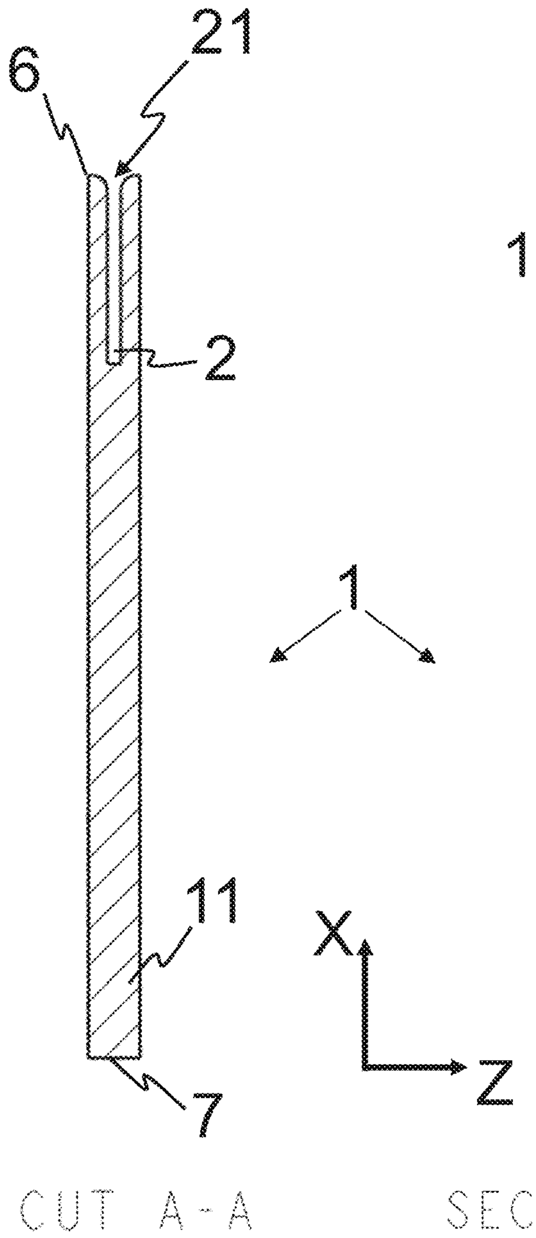
FIG. 7A illustrates a schematic first cut view of an example cuvette along a cut line A-A as disclosed herein.
Figure 7B:
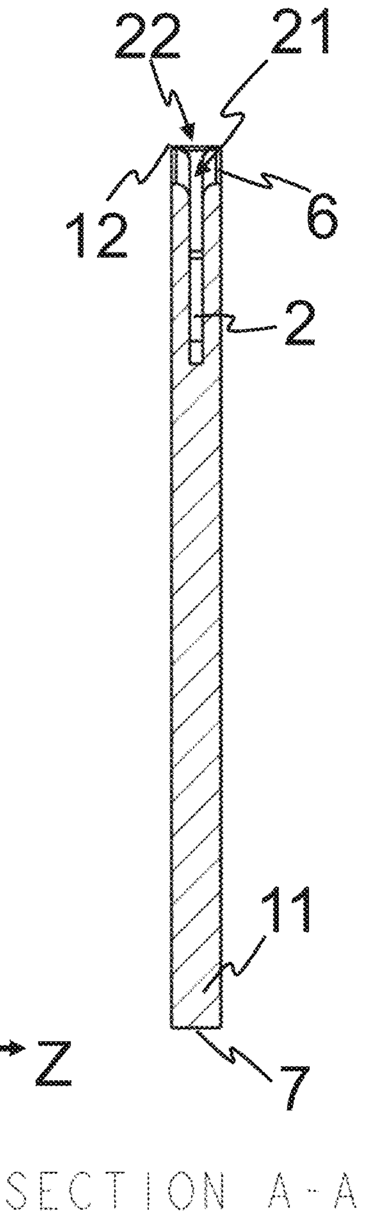
FIG. 7B illustrates a schematic first cross-section view of an example cuvette along the cut line A-A as disclosed herein.

FIG. 7A shows a cut view and FIG. 7B shows a section view of the cuvette 1 through the cutting plane A-A. As can be seen in the cut view of FIG. 7A, the sampling cavity 2 is arranged in the main body 11 at the first end 6 of the cuvette 1. The sampling cavity 2 has the opening 21 through the outer side wall of the cuvette 1 at the first end 6.

The section view of FIG. 7B shows the cross section of the cuvette seen facing the tip 12 of the cuvette 1. As can be seen, the opening 21 of the sampling cavity 2 extends over the entire width of the sampling cavity 2 to the inlet 22 arranged at the tip 12.

Figures 8A, 8B:
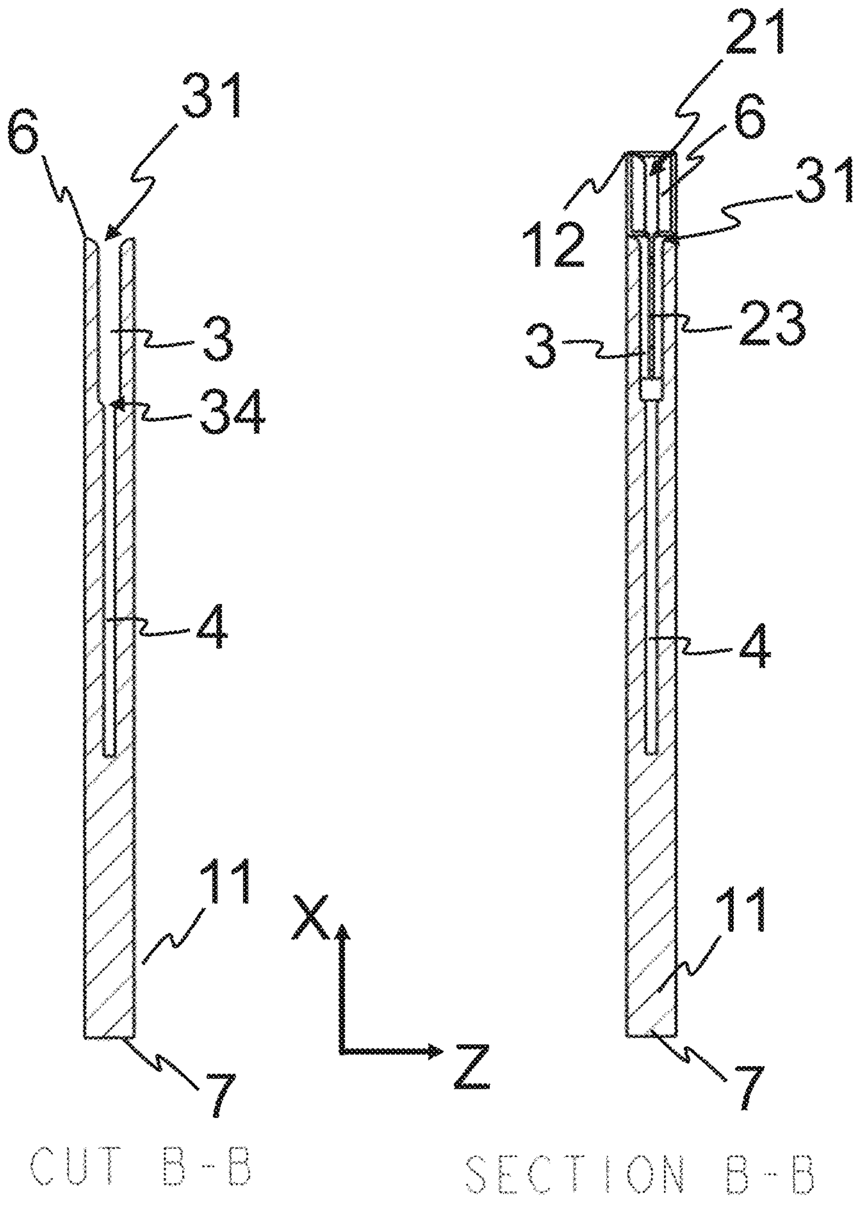
FIG. 8A illustrates a schematic second cut view of an example cuvette along a cut line B-B as disclosed herein.
FIG. 8B illustrates a schematic second cross-section view of an example cuvette along the cut line B-B as disclosed herein.

FIG. 8A shows a cut view and FIG. 8B shows a section view of the cuvette 1 through the cutting plane B-B. The venting cavity 3 is arranged at the first end 6 of the cuvette 1 and extends between the first end 6 and the sample analysis cavity 4. The sample analysis cavity 4 extends in the longitudinal direction from the venting cavity 3 towards the second end 7 of the cuvette 1. As can be seen in the cut view in FIG. 8A, the sample analysis cavity 4 is narrower than the venting cavity 3, such as has a smaller height than the venting cavity 3. Due to the sample analysis cavity 4 having a smaller height than the venting cavity 3, the first capillary force is higher than the second capillary force. Thereby, a transport of the blood sample from the venting cavity 3, through the second interface 34 to the sample analysis cavity 4 can be enhanced as the first capillary force will suck the blood sample into the sample analysis cavity 4. The first capillary force being higher than the second capillary force further prevents the fluid to flow from the sample analysis cavity 4 back to the venting cavity 3.

The section view of FIG. 8B shows the cross section of the cuvette seen facing the tip 12 of the cuvette 1. As can be seen, the opening 21 of the sampling cavity 2 and the outlet 31 of the venting cavity 3 are connected, so that the first outer wall of the cuvette at the first end 6 is open over the entire length of the sampling cavity 2 and the venting cavity 3. This allows a shaping tool having on a common shaping core for all the cavities to be removed through the opening 21 and the outlet 31. The first interface 23 is arranged in the longitudinal direction of the cuvette and separates the sampling cavity 2 from the venting cavity 3. As can be seen in FIG. 5B, the height of the opening of the first interface 31 is smaller than the height of the sample analysis cavity 4 and the sampling cavity 2.

Figure 9:
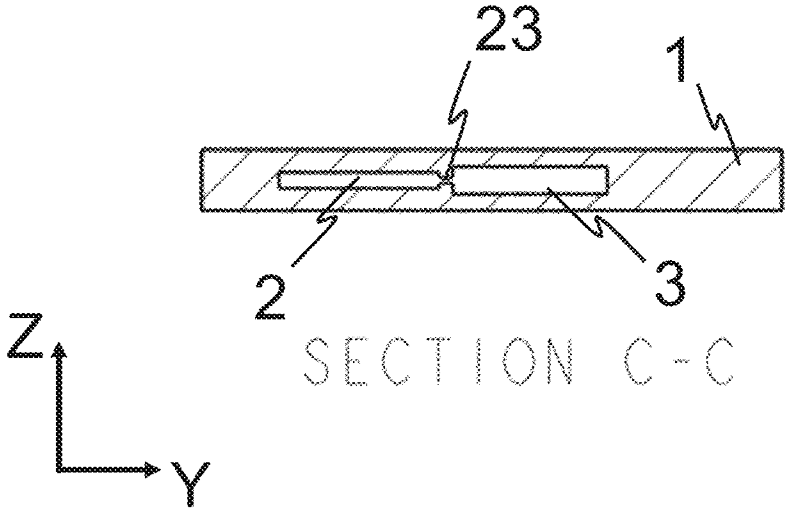
FIG. 9 illustrates a schematic third cross-section view of an example cuvette along a cut line C-C as disclosed herein.

FIG. 9 shows a section view of the cuvette 1 through the cutting plane C-C. As previously discussed, the height of the sampling cavity 3 is smaller than the height of the venting cavity 3. Due to the sampling cavity 2 having a smaller height than the venting cavity, the third capillary force in the sampling cavity 2 is higher than the second capillary force. Thereby, a blood sample in the sampling cavity can be prevented from spontaneously flowing from the sampling cavity 2 to the venting cavity 3. The sampling cavity 2 and the venting cavity 3 may be connected by the first interface 23. The height of the first interface 23 may have a smaller height than both the sampling cavity 2 and the venting cavity 3. The first interface 23 may thus be an area adjacent to the sampling cavity 2 that has a very narrow thickness to further ensure that there is no capillary transport from the sampling cavity 2 to the venting cavity 3. The first interface may thus act as a lock preventing the blood sample to flow from the sampling cavity 2 to the venting cavity 3. To transport the blood sample to the venting cavity 3, a centrifugal force can be applied to the cuvette 1. When the centrifugal force being applied to the cuvette 1 overcomes the third capillary force the blood sample may leave the sampling cavity 2 via the first interface 23 and may enter the venting cavity 3, from where the blood sample may enter the sample analysis cavity 4.

Figure 10:
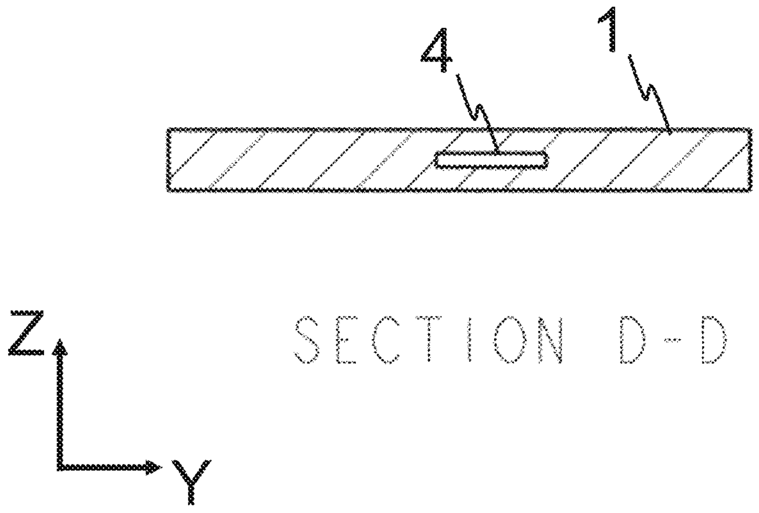
FIG. 10 illustrates a schematic fourth cross-section view of an example cuvette along a cut line D-D as disclosed herein.

FIG. 10 shows a section view of the cuvette 1 through the cutting plane D-D. As can be seen in FIG. 10 when comparing it to the section view C-C in FIG. 9, the cross-section area of the sample analysis cavity 3, such as the height and the width of the of the sample analysis cavity 3 is smaller than the cross-section area of the venting cavity 3, thereby causing the sampling cavity 4 to have a higher capillary force than the venting cavity 3. Further, the smaller height and smaller width of the sample analysis cavity 4 compared to the height and the width of the venting cavity 3 allows the parts of the shaping tool being furthest inside the main body member 11 of the cuvette 1 during manufacturing, such as the parts shaping the sample analysis cavity 4, to be removed via the wider outer sections of the cuvette 1, such as via the wider venting cavity 3.

It shall be noted that the features mentioned in the embodiments described in FIGS. 4-10 are not restricted to these specific embodiments. Any features of the cuvette and the components comprised therein and mentioned in relation to the FIGS. 4-10, such as dimensions of the cuvette and/or the cavities, are thus also applicable to the cuvette described in relation to the method and/or the analyzer for analyzing a blood sample in FIGS. 1 to 3, and vice versa.

Examples of methods and analyzer according to the disclosure are set out in the following items:

Item 1. A method for analyzing a blood sample, the method comprising:
- arranging (S102) a cuvette comprising a sampling cavity and a sample analysis cavity on a rotatable member, wherein the sampling cavity comprises a blood sample to be analyzed;
- rotating (S110) the rotatable member at a first speed in a first rotation cycle for transfer of the blood sample from the sampling cavity to the sample analysis cavity;
- rotating (S116) the rotatable member at a second speed in a second rotation cycle after the first rotation cycle for separating blood parts from plasma in the blood sample;
- obtaining (S118), using a photometer, during the second rotation cycle, second absorbance data indicative of absorbance in the plasma;
- determining (S119), based on the second absorbance data, a second blood parameter being a plasma free hemoglobin level of the blood sample; and
- providing (S120) an output indicative of the second blood parameter.

Item 2. The method according to Item 1, wherein the method comprises:
- prior to the first rotation cycle, rotating (S104) the rotatable member at an initial speed in an initial rotation cycle, wherein the initial speed is insufficient for transfer of the blood sample from the sampling cavity to the sample analysis cavity;
- obtaining (S106), using the photometer and during the initial rotation cycle, initial absorbance data indicative of an absorbance in the sample analysis cavity of the cuvette; and
- determining (S108), based on the initial absorbance data, a cuvette parameter being a contamination level associated with the cuvette.

Item 3. The method according to any one of the previous Items, wherein obtaining (S118) comprises continuously obtaining (S118A) the second absorbance data during the second rotation cycle, and wherein the method comprises:

upon detecting a stabilization of the second absorbance data, ending the continuous obtaining (S118A) of the second absorbance data.

Item 4. The method according to any one of the previous Items, wherein the method comprises:

obtaining (S112), using the photometer and during the first rotation cycle, first absorbance data indicative of an absorbance in the blood sample in the sample analysis cavity of the cuvette, determining (S114), based on the first absorbance data, a first blood parameter being a total hemoglobin level of the blood sample.

Item 5. The method according to Item 4, wherein the method comprises:

obtaining (S121), using the photometer, during the second rotation cycle, third absorbance data indicative of a separation time of red blood cells from the plasma;

determining (S122), based on the third absorbance data and the first absorbance data, a third blood parameter being an erythrocyte sedimentation rate of the blood sample; and providing (S123) an output indicative of the third blood parameter.

Item 6. The method according to any one of the previous Items, wherein the method comprises:

obtaining (S124), using an imaging device, after the second rotation cycle, first image data representing an image of at least a part of the blood sample in the sample analysis cavity;

determining (S126), based on the first image data, a fourth blood parameter being a hematocrit level of the blood sample; and providing (S128) an output indicative of the fourth blood parameter.

Item 7. The method according to any one of the previous Items, wherein the method comprises:

after the second rotation cycle, rotating (S130) the rotatable member at a third speed in a third rotation cycle, wherein the third speed is higher than the first speed, the second speed and the initial speed, obtaining (S132), using the photometer and during the third rotation cycle, fourth absorbance data indicative of an absorbance in the blood sample in the sample analysis cavity of the cuvette, and determining (S134), based on the fourth absorbance data, a fifth blood parameter being a second plasma free hemoglobin level indicating fragile blood cells of the blood sample.

Item 8. The method according to any one of the previous Items, wherein obtaining initial absorbance data, first absorbance data, second absorbance data, third absorbance data or fourth absorbance data comprises measuring absorbance using more than two wavelengths.

Item 9. The method according to any one of the previous Items, wherein obtaining initial absorbance data, first absorbance data, second absorbance data, third absorbance data or fourth absorbance data comprises measuring absorbance data during a plurality of revolutions of the rotatable member.

Item 10. The method according to any one of the previous Items, wherein determining one or more of the first blood parameter, the second blood parameter, the third blood parameter, the fourth blood parameter, the fifth parameter and the cuvette parameter comprises integrating absorbance data obtained during a plurality of revolutions of the rotatable member.

Item 11. The method according to any one of the previous Items, wherein the blood parts separated from the plasma are one or more of blood cells, red blood cells, white blood cells, fibrinogen, buffy coat, and lipids.

Item 12. A blood analyzer comprising a housing, a rotatable member, a photometer, and a controller, the rotatable member being rotatably arranged in the housing and comprising a receptacle for receiving a cuvette comprising a sampling cavity and a sample analysis cavity, the sampling cavity of the cuvette comprising a blood sample to be analyzed;

the photometer being configured to obtain absorbance data associated with the sample analysis cavity of the cuvette;

wherein the controller is configured to:

rotate the rotatable member at a first speed in a first rotation cycle for transfer of the blood sample from the sampling cavity to the sample analysis cavity;

rotate the rotatable member at a second speed in a second rotation cycle after the first rotation cycle for separating blood parts from plasma in the blood sample;

control the photometer to obtain, during the second rotation cycle, second absorbance data indicative of absorbance in the plasma of the separated blood sample; and determine, based on the second absorbance data, a second blood parameter being a plasma free hemoglobin level of the blood sample; and provide an output indicative of the second blood parameter.

Item 13. The blood analyzer according to Item 12, wherein the controller is configured to:

prior to the first rotation cycle, rotate the rotatable member at an initial speed in an initial rotation cycle, wherein the initial speed is insufficient for transfer of the blood sample from the sampling cavity to the sample analysis cavity;

control the photometer to obtain, during the initial rotation cycle, initial absorbance data indicative of an absorbance in the sample analysis cavity of the cuvette; and determine, based on the initial absorbance data, a cuvette parameter being a contamination level associated with the cuvette, and provide an output indicative of the cuvette parameter.

Item 14. The blood analyzer according to Item 12 or 13, wherein the controller is configured to control the photometer to continuously obtain the second absorbance data during the second rotation cycle, and, upon detecting a stabilization of the second absorbance data, control the photometer to end the continuous obtaining of the second absorbance data.

Item 15. The blood analyzer according to Item 12 to 14, wherein the controller is configured to:

control the photometer to obtain, during the first rotation cycle, first absorbance data indicative of an absorbance in the blood sample in the sample analysis cavity of the cuvette; and determine, based on the first absorbance data, a first blood parameter being total hemoglobin level of the blood sample, and provide an output indicative of the first blood parameter.

Item 16. The blood analyzer according to Item 15, wherein the controller is configured to:
- control the photometer to obtain, during the second rotation cycle, third absorbance data indicative of a separation time of red blood cells from the plasma in the sample analysis cavity of the cuvette;
- determine, based on the third absorbance data and the first absorbance data, a third blood parameter being an erythrocyte sedimentation rate of the blood sample in the sample analysis cavity of the cuvette; and
- provide an output indicative of the third blood parameter.

Item 17. The blood analyzer according to any one of the Items 12 to 16, wherein analyzer comprises an imaging device and wherein the controller is configured to:
- control the imaging device to obtain, after the second rotation cycle, first image data representing an image of at least a part of the blood sample in the sample analysis cavity of the cuvette;
- determine, based on the first image data, a fourth blood parameter being the hematocrit level of the blood sample; and
- provide an output indicative of the fourth blood parameter Item 18. The blood analyzer according to any one of the Items 12 to 17, wherein the controller is configured to:
- after the second rotation cycle, rotate the rotatable member at a third speed in a third rotation cycle, wherein the third speed is higher than the first speed, the second speed and the initial speed;
- control the photometer to obtain, during the third rotation cycle, fourth absorbance data indicative of an absorbance in the blood sample in the sample analysis cavity of the cuvette; and
- determine, based on the fourth absorbance data, a fifth blood parameter being a second plasma free hemoglobin level indicating fragile blood cells of the blood sample.

Item 19. The blood analyzer according to any one of the Items 12 to 18, wherein the photometer is configured to obtain initial absorbance data, first absorbance data, second absorbance data, third absorbance data, or fifth absorbance by measuring absorbance using more than two wavelengths.

Item 20. The blood analyzer according to Item 19, wherein the photometer comprises at least two light sources and at least two corresponding optical sensors, each light source emitting light at a different wavelength.

Item 21. The blood analyzer according to Item 20, wherein the at least two light sources are Light Emitting Diodes.

Item 22. The blood analyzer according to any one of the Items 12 to 21, wherein the controller is configured to control the photometer and any imaging device, respectively, to measure initial absorbance data, first absorbance data, second absorbance data, third absorbance data, first image data, or fourth absorbance data during a plurality of revolutions of the rotatable member.

Item 23. The blood analyzer according to Item 22, wherein the controller is configured to integrate absorbance data obtained by the photometer during the plurality of revolutions of the rotatable member.

Item 24. The blood analyzer according to any one of the Items 12 to 23, wherein the blood parts separated from the plasma are one or more of blood cells, red blood cells, white blood cells, fibrinogen, buffy coat, and lipids.

The use of the terms “first”, “second”, “third” and “fourth”, “primary”, “secondary”, “tertiary” etc. does not imply any particular order, but are included to identify individual elements. Moreover, the use of the terms “first”, “second”, “third” and “fourth”, “primary”, “secondary”, “tertiary” etc. does not denote any order or importance, but rather the terms “first”, “second”, “third” and “fourth”, “primary”, “secondary”, “tertiary” etc. are used to distinguish one element from another. Note that the words “first”, “second”, “third” and “fourth”, “primary”, “secondary”, “tertiary” etc. are used here and elsewhere for labelling purposes only and are not intended to denote any specific spatial or temporal ordering. Furthermore, the labelling of a first element does not imply the presence of a second element and vice versa.

It is to be noted that the word “comprising” does not necessarily exclude the presence of other elements or steps than those listed.

It is to be noted that the words “a” or “an” preceding an element do not exclude the presence of a plurality of such elements.

Although features have been shown and described, it will be understood that they are not intended to limit the claimed disclosure, and it will be made obvious to those skilled in the art that various changes and modifications may be made without departing from the scope of the claimed disclosure. The specification and drawings are, accordingly to be regarded in an illustrative rather than restrictive sense. The claimed disclosure is intended to cover all alternatives, modifications, and equivalents.

It may be appreciated that FIGS. 1-10 comprise some features, components or method steps which are illustrated with a solid line and some features, components or method steps which are illustrated with a dashed line. Features, components, or method steps illustrated with a solid line are features, components or method steps which are comprised in the broadest example. Features, components, or method steps which are comprised in a dashed line are examples which may be comprised in, or a part of, or are further features, components or method steps which may be taken in addition to features, components or method steps of the solid line examples. It should be appreciated that not all of the method steps need to be performed. Features, components or method steps which are comprised in a dashed line may be considered optional.

It is to be noted that the word “comprising” does not necessarily exclude the presence of other elements or steps than those listed.

It is to be noted that the words “a” or “an” preceding an element do not exclude the presence of a plurality of such elements.

The invention claimed is:

1. A method for analyzing a blood sample, the method comprising:
- arranging a cuvette comprising a sampling cavity and a sample analysis cavity on a rotatable member, wherein the sampling cavity comprises the blood sample to be analyzed;
- prior to a first rotation cycle, rotating the rotatable member at an initial speed in an initial rotation cycle, wherein the initial speed is insufficient for transfer of the blood sample from the sampling cavity to the sample analysis cavity, obtaining, using a photometer, during the initial rotation cycle, initial absorbance data indicative of an absorbance in or through the sample analysis cavity of the cuvette, determining, based on the initial absorbance data, a cuvette parameter associated with the cuvette, providing an output indicative of the cuvette parameter, rotating the rotatable member at the first speed in the first rotation cycle for transfer of the blood sample from the sampling cavity to the sample analysis cavity;

rotating the rotatable member at a second speed in a second rotation cycle after the first rotation cycle for separating blood parts from plasma in the blood sample;

obtaining, using the photometer, during the second rotation cycle, second absorbance data indicative of absorbance in the plasma;

determining, based on the second absorbance data, a second blood parameter being a plasma free hemoglobin level of the blood sample; and providing an output indicative of the second blood parameter.

2. The method according to claim 1, wherein the cuvette parameter is indicative of one or more of:

a contamination level associated with the cuvette, absorbance data of the empty cuvette, and a presence of a cuvette in the receptacle of the rotatable member.

3. The method according to claim 1, wherein the obtaining the second absorbance data comprises continuously obtaining the second absorbance data during the second rotation cycle, and wherein the method further comprises:

upon detecting a stabilization of the second absorbance data, ending the continuous obtaining of the second absorbance data.

4. The method according to claim 1, wherein the method further comprises:

obtaining, using the photometer and during the first rotation cycle, first absorbance data indicative of an absorbance in the blood sample in the sample analysis cavity of the cuvette, and determining, based on the first absorbance data, a first blood parameter being a total hemoglobin level of the blood sample.

5. The method according to claim 4, wherein the method further comprises:

obtaining, using the photometer, during the second rotation cycle, third absorbance data indicative of a separation time of red blood cells from the plasma;

determining, based on the third absorbance data and the first absorbance data, a third blood parameter being an erythrocyte sedimentation rate of the blood sample; and providing an output indicative of the third blood parameter.

6. The method according to claim 1, wherein the method further comprises:

obtaining, using an imaging device, after the second rotation cycle, first image data representing an image of at least a part of the blood sample in the sample analysis cavity;

determining, based on the first image data, a fourth blood parameter being a hematocrit level of the blood sample; and providing an output indicative of the fourth blood parameter.

7. The method according to claim 1, wherein the method further comprises:

after the second rotation cycle, rotating the rotatable member at a third speed in a third rotation cycle, wherein the third speed is higher than the first speed, the second speed and the initial speed, obtaining, using the photometer and during the third rotation cycle, fourth absorbance data indicative of an absorbance in the blood sample in the sample analysis cavity of the cuvette, and determining, based on the fourth absorbance data, a fifth blood parameter being a second plasma free hemoglobin level indicating fragile blood cells of the blood sample.

8. The method according to claim 1, wherein the obtaining the initial absorbance data and the second absorbance data comprises measuring absorbance using more than two wavelengths.

9. The method according to claim 5, wherein the obtaining initial absorbance data, the first absorbance data, the second absorbance data, or the third absorbance data comprises measuring absorbance data during a plurality of revolutions of the rotatable member.

10. The method according to claim 5, wherein the determining one or more of the first blood parameter, the cuvette parameter, the second blood parameter, or the third blood parameter comprises integrating absorbance data obtained during a plurality of revolutions of the rotatable member.

11. The method according to claim 1, wherein the blood parts separated from the plasma are one or more of blood cells, red blood cells, white blood cells, fibrinogen, buffy coat, and lipids.

12. A blood analyzer comprising a housing, a rotatable member, a photometer, and a controller, the rotatable member being rotatably arranged in the housing and comprising a receptacle for receiving a cuvette comprising a sampling cavity and a sample analysis cavity, the sampling cavity of the cuvette comprising a blood sample to be analyzed;

the photometer being configured to obtain absorbance data associated with the sample analysis cavity of the cuvette;

wherein the controller is configured to:

prior to a first rotation cycle, rotate the rotatable member at an initial speed in an initial rotation cycle, wherein the initial speed is insufficient for transfer of the blood sample from the sampling cavity to the sample analysis cavity, control the photometer to obtain, during the initial rotation cycle, initial absorbance data indicative of an absorbance in the sample analysis cavity of the cuvette;

determine, based on the initial absorbance data, a cuvette parameter associated with the cuvette, and provide an output indicative of the cuvette parameter, rotate the rotatable member at a first speed in the first rotation cycle for transfer of the blood sample from the sampling cavity to the sample analysis cavity;

rotate the rotatable member at a second speed in a second rotation cycle after the first rotation cycle for separating blood parts from plasma in the blood sample;

control the photometer to obtain, during the second rotation cycle, second absorbance data indicative of absorbance in the plasma of the separated blood sample; and determine, based on the second absorbance data, a second blood parameter being a plasma free hemoglobin level of the blood sample; and provide an output indicative of the second blood parameter.

13. The blood analyzer according to claim 12, wherein the controller is configured to control the photometer to continuously obtain the second absorbance data during the second rotation cycle, and, upon detecting a stabilization of the second absorbance data, control the photometer to end the continuous obtaining of the second absorbance data.

14. The blood analyzer according to claim 12, wherein the controller is further configured to:

control the photometer to obtain, during the first rotation cycle, first absorbance data indicative of an absorbance in the blood sample in the sample analysis cavity of the cuvette; and determine, based on the first absorbance data, a first blood parameter being total hemoglobin level of the blood sample, and provide an output indicative of the first blood parameter.

15. The blood analyzer according to claim 14, wherein the controller is further configured to:

control the photometer to obtain, during the second rotation cycle, third absorbance data indicative of a separation time of red blood cells from the plasma in the sample analysis cavity of the cuvette;

determine, based on the third absorbance data and the first absorbance data, a third blood parameter being an erythrocyte sedimentation rate of the blood sample in the sample analysis cavity of the cuvette; and provide an output indicative of the third blood parameter.

16. The blood analyzer according to claim 12, wherein the blood analyzer further comprises an imaging device and wherein the controller is further configured to:

control the imaging device to obtain, after the second rotation cycle, first image data representing an image of at least a part of the blood sample in the sample analysis cavity of the cuvette;

determine, based on the first image data, a fourth blood parameter being the hematocrit level of the blood sample; and provide an output indicative of the fourth blood parameter.

17. The blood analyzer according to claim 12, wherein the controller is further configured to:

after the second rotation cycle, rotate the rotatable member at a third speed in a third rotation cycle, wherein the third speed is higher than the first speed, the second speed and the initial speed;

control the photometer to obtain, during the third rotation cycle, fourth absorbance data indicative of an absorbance in the blood sample in the sample analysis cavity of the cuvette; and determine, based on the fourth absorbance data, a fifth blood parameter being a second plasma free hemoglobin level indicating fragile blood cells of the blood sample.

18. The blood analyzer according to claim 15, wherein the photometer is configured to obtain the initial absorbance data, the first absorbance data, the second absorbance data, or the third absorbance data by measuring absorbance using more than two wavelengths.

19. The blood analyzer according to claim 18, wherein the photometer comprises at least two light sources and at least two corresponding optical sensors, each light source emitting light at a different wavelength.

20. The blood analyzer according to claim 19, wherein the at least two light sources are Light Emitting Diodes (LEDs).

21. The blood analyzer according to claim 15, wherein the controller is configured to control the photometer and any imaging device, respectively, to measure the initial absorbance data, the first absorbance data, the second absorbance data, or the third absorbance data during a plurality of revolutions of the rotatable member.

22. The blood analyzer according to claim 21, wherein the controller is configured to integrate absorbance data obtained by the photometer during the plurality of revolutions of the rotatable member.

23. The blood analyzer according to claim 12, wherein the blood parts separated from the plasma are one or more of blood cells, red blood cells, white blood cells, fibrinogen, buffy coat, and lipids.

* * * * *